US007977108B2

(12) United States Patent
Newhouse et al.

(10) Patent No.: US 7,977,108 B2
(45) Date of Patent: Jul. 12, 2011

(54) METHOD FOR DETECTING A MUTATION IN A REPETITIVE NUCLEIC ACID SEQUENCE

(75) Inventors: Christopher D. Newhouse, Alameda, CA (US); Stephen Gordon Will, Oakland, CA (US); Amar P. Gupta, Danville, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 363 days.

(21) Appl. No.: 11/487,156

(22) Filed: Jul. 13, 2006

(65) Prior Publication Data
US 2007/0031870 A1    Feb. 8, 2007

Related U.S. Application Data

(60) Provisional application No. 60/702,501, filed on Jul. 25, 2005.

(51) Int. Cl.
G01N 33/00 (2006.01)
C12Q 1/68 (2006.01)
C12M 1/34 (2006.01)
C07H 21/04 (2006.01)
C07H 21/00 (2006.01)

(52) U.S. Cl. .......... 436/94; 435/6; 435/287.2; 536/23.1; 536/24.3; 536/25.32

(58) Field of Classification Search .................. None
See application file for complete search history.

(56) References Cited

U.S. PATENT DOCUMENTS

| | | | |
|---|---|---|---|
| 5,210,015 A | 5/1993 | Gelfand et al. | |
| 5,538,848 A | 7/1996 | Livak et al. | |
| 5,994,056 A | 11/1999 | Higuchi | |
| 6,171,785 B1 | 1/2001 | Higuchi | |
| 6,238,862 B1 | 5/2001 | McGall et al. | |
| 7,785,776 B2* | 8/2010 | Wittwer et al. ............. | 435/6 |
| 2001/0044531 A1 | 11/2001 | McGall et al. | |
| 2002/0119455 A1* | 8/2002 | Chan ............................. | 435/6 |
| 2003/0165941 A1 | 9/2003 | Gjerde et al. ............... | 435/6 |
| 2004/0229349 A1* | 11/2004 | Daridon ..................... | 435/305.2 |
| 2006/0286570 A1* | 12/2006 | Rowlen et al. ............. | 435/6 |
| 2007/0009954 A1* | 1/2007 | Wang et al. ................. | 435/6 |
| 2007/0031829 A1* | 2/2007 | Yasuno et al. .............. | 435/6 |
| 2007/0042400 A1* | 2/2007 | Choi et al. ................... | 435/6 |
| 2007/0042419 A1* | 2/2007 | Barany et al. .............. | 435/6 |

FOREIGN PATENT DOCUMENTS

| | | |
|---|---|---|
| EP | 1 207 210 A1 | 5/2002 |
| EP | 1 362 928 A2 | 11/2003 |
| WO | WO 01/16150 A2 | 3/2001 |

OTHER PUBLICATIONS

Zhang et al., Bioinformatics, 2003, vol. 19, No. 1, pp. 14-21.*
Burggraf, S., et al., 2002, Genotyping of the Methionine-Valine Polymorphism at Codon 129 of the Human Prion Protein my Melting Point Analysis of Fluorescently labeled Hybridization Probes. *Rapid Cycle Real-Time PCR: Methods and Applications*, 115-127.
Dietmaier, W., et al., 2001, Detection of Microsatellite Instability by Real Time PCR and Hybridization Probe Melting Point Analysis. *Laboratory Investigation*, 81 (10): 1435-1456.
EP Appln 06015300 Search Report, Dec. 8, 2006, EP.
Barone, A., et al. 2001, "Novel Nucleoside Triphosphate Analogs for the Enzymatic Labeling of Nucleic Acids", *Nucleosides, Nucleotides & Nucleic Acids*, 20 (4-7): 1141-1145.
Chauviere, G., et al., 2000, << Nucleophilic Substitution studies on nitroimidazoles, and applications to the synthesis of biologically active compounds', *J. Heterocyclic Chem.* 37 :119-126.
Durland, R., et al., 1995, "Azole substituted oligonucleotides promote antiparallel triplex formation at non-homopurine duplex targets", *Nucleic Acids Research*, 23(4): 647-653.
Ellis, G., 2000, :Chromans and Tocopherols, *The Chemistry of Heterocyclic Compounds*, 36(2) 182-184.
Holland, P., et al., 1991, "Detection of Specific polymerase chain reaction product by utilizing the 5'→3' exonuclease activity of *Thermus aquaticus* DNA polymerase", *Proc. Natl Acad. Sci.*, 88: 7276-7280.
Kulkarni, S., et al., 1987, "Nucleophillic Displacements of Imidazoles, I Oxygen, nitrogen and carbon nucleophiles", *Aust J Chem*, 40: 1399-1413.
Kumar, A., 1988, "Nonradioactive Labeling of Synthetic Oligonucleotide Probes with Terminal Deoxynucleotidyl Transferases", *Analytical Biochemistry* 169: 376-382.
Mourabit, A, et al., 1996, New C2 symmetrical and semi-symmetrical substituted imidazolium ribonucleoside. Imidazolic nucleosides analogues', *Tetrahedron Asymmetry*, 7(12) 3455-3464.
Nagarajan, K., et al., 1982, Nitroimidazoles: Part IV—1-sulphonyl (carbamoyl/thiocarbamoyl)-3-(1-methyl-5-nitroimidazol-2-yl)-2-imidazolidnones, *Indian Journal of Chemistry*, 21B: 928-940.
Pochet, S., et al., 1990, Synthesis and emzymatic polymerization of 5-amino-1-(2-deoxy-β-D-Ribofuranosyl) imidazole-4-carboxamide-5'-triphosphate', *Nucleic Acids Reserach*, 18(23): 7127-7131.
Pochet, S., et al., 1995, Enzymatic synthesis of 1-(2-deoxy-β-D-Ribofuranosyl) imidazole-4-carboxamide, a simplified DNA building block', *Bioorganic & Medicinal Chemistry Letters*, 5(15): 1679-1685.
Suzuki, T., et al., 2000, "Formation of 2'-Deoxyoxanosine from 2'-Deoxyguanosine and nitrous acid: mechanism and intermediates", *Nucleic Acids Research*, 28(2): 544-551.
Suzuki, T., et al., 2000, Identification and Characterization of a Reaction Product of 2'-Deoxyoxanosine with Glycine>>, *Chem. Res. Toxicol*, 13: 227-230.
Dietmaier, W., 2001, "Detection of microsatellite instability by real-time PCR and hybridization probe melting point analysis," Laboratory Investigation, 81(10):1453-1456.

(Continued)

*Primary Examiner* — Bradley L Sisson
(74) *Attorney, Agent, or Firm* — Olga Kay; Vivien M. Banholzer; David J. Chang

(57) ABSTRACT

The present invention provides methods and probe nucleic acids for detecting mutant forms of target nucleic acids that comprise repetitive nucleotide sequences. In certain embodiments, for example, these approaches and reagents can be used to detect instability in regions of genomic DNA that include microsatellite markers. The invention also provides related reaction mixtures, systems, and kits.

2 Claims, 15 Drawing Sheets

OTHER PUBLICATIONS

Bloemeke, Brunhilde, et al., (1999), "Identification of N-Acetyltransferase 2 Genotypes by Continuous Monitoring of Fluorogenic Hybridization Probes", Analytical Biochemistry, 275:93-97.

Cane, Patricia A., et al., (1999), "Use of Real-Time PCR and Fluorimetry to Detect Lamivudine Resistance-Associated Mutations in Hepatitis B Virus", Antimicrobial Agents and Chemotherapy, 43(7):1600-1608.

Schutz, Ekkehard and Von Ahsen, Nicolas, (1999), "Spreadsheet Software for Thermodynamic Melting Point Prediction of Oligonucleotide Hybridization with and without Mismatches", BioTechniques, 27:1218-1224.

* cited by examiner

Nucleotide Sequences All sequences are written 5' to 3'

| SEQ ID NO: | Description | SEQUENCE |
|---|---|---|
| 1 | Oligonucleotide Probe | CCUUUUUUUUUUUUUUUUUUUACCTG |
| 2 | Oligonucleotide Probe | TTTTTTTTTTTTTTTTTTTTTT |
| 3 | Oligonucleotide Probe | CCUUUUUUUUUUUUUUUUUUUACCTG |
| 4 | Oligonucleotide Probe | CCUUUUUUUUUUUUUUUUUUUACCTG |
| 5 | Oligonucleotide Probe | TTAACCTTTTCAGGTAAAAAAAAAAAAAAAAAAAAGGTTAAAAATGTTG |
| 6 | Oligonucleotide Probe | TAACCTTTTCAGGTAAAAAAAAAAAAAAAAAAAAGGGTTAAAAATGTTG |
| 7 | Oligonucleotide Probe | TAACCTTTTCAGGTAAAAAAAAAAAAAAAAAAAAGGGTTATGTTG |

FIG. 6

| SEQ ID NO: | Description | SEQUENCE |
|---|---|---|
| 8 | Oligonucleotide Probe | TAACCTTTTCAGGTAAAAAAAAAAAAAAAAGGGTTATGTT G  26 |
| 9 | Oligonucleotide Probe | TAACCTTTTCAGGTAAAAAAAAAAAAAAGGGTTATGTTG  27 |
| 10 | Oligonucleotide Probe | FCCUUUUUUUUUUUUUUUUUUUUUUUACCTGP  CDN 28 |
| 11 | Oligonucleotide Probe | FTTTTTTTTTTTTTTTTTTTTTTP  CDN 29 |
| 12 | Oligonucleotide Probe | FCCUUUUUUUUUUUUUUUUUUUUACCTGP  CDN 30 |
| 13 | Oligonucleotide Probe | FCCUUUUUUUUUUUUUUUUUUUACCTGP |
| 14 | Oligonucleotide Probe | TAACCTTTTCAGGTAAAAAAAAAAAAAAGGGTAAAATGTTG |
| 15 | Oligonucleotide Probe | TAACCTTTTCAGGTAAAAAAAAAAAAAAAGGGTAAAAATGTTG |

FIG. 6 (continued)

| SEQ ID NO: | Description | SEQUENCE |
|---|---|---|
| 16 | Oligonucleotide Probe | TAACCTTTTTCAGGTAAAAAAAAAAAAAAAAAAAAGGGTTAAA AATGTTG |
| 17 | BAT-25 Locus primer | TCGCCTCCAAGAATGTAAGT |
| 18 | BAT-25 Locus primer | TCTGCATTTTAACTATGGCT |
| 19 | BAT-25 Locus primer | ATTCTGCATTTTAACTATGGCTCT |
| 20 | BAT-26 Locus primer | TGATTCCAATCATAGCCACA |
| 21 | BAT-25 Locus primer | CCTGGAAGAACCAATGCTTA |
| 22 | BAT-26 Locus primer | TTGAGCCCAGAAAGTTTGAG |
| 23 | BAT-26 Locus primer | AACCAATCAACATTTTAACCCTT |
| 24 | BAT-40 Locus primer | GCTTGCAGACAGCCTATTGT |

FIG. 6 (continued)

| SEQ ID NO: | Description | SEQUENCE |
|---|---|---|
| 25 | BAT-40 Locus primer | GTAGAGCAAGACCACCTTG |
| 26 | D7S1808 Locus primer | CAGAACAAACAAATGGGGAG |
| 27 | D7S1808 Locus primer | CCAAATAAGACTCAGGACGC |
| 28 | D7S1808 Locus primer | GGAGGAAAAGTCTAAACGTGAAT |
| 29 | D7S1808 Locus primer | ATTGGCCTGATGTGTTTGTTACT |
| 30 | D10S1426 Locus primer | TTGGTGGTGTCATCCTCTTT |
| 31 | D10S1426 Locus primer | CTCTTAACTGATTGGCCGA |
| 32 | D10S1426 Locus primer | CCCCTTGGTGGTGTCATCCT |
| 33 | D10S1426 Locus primer | ATTGCCGATCCTGAAGCAATAGC |

FIG. 6 (continued)

| SEQ ID NO: | Description | SEQUENCE |
|---|---|---|
| 34 | D3S2432 Locus primer | GGCAGGGCAGGTGGATAGACA |
| 35 | D3S2432 Locus primer | ACACTAAACAAGCATAGTCAGGC |
| 36 | D3S2432 Locus primer | ATTGTTTGCATGTGAAACAGGTCA |
| 37 | D7S3046 Locus primer | ACATACGGATGAATGGATGG |
| 38 | D7S3046 Locus primer | TATAACCTCTCTCCCTATCTCCC |
| 39 | D7S3046 Locus primer | ATTTCTCATAACCTCTCTCCCTATCT |
| 40 | D7S3046 Locus primer | ATTTCTCTATAACCTCTCTCCCTATCT |
| 41 | D7S3070 Locus primer | CCCCCATGAGTTATTCCTCT |
| 42 | D7S3070 Locus primer | GGAAGCCAAATGTTGAATTG |

FIG. 6 (continued)

| SEQ ID NO: | Description | SEQUENCE |
|---|---|---|
| 43 | D7S3070 Locus primer | CATTTCTTCTGCCCCATGA |
| 44 | D7S3070 Locus primer | ATTTGACAGCTGAAAGGTGCAGATG |
| 45 | MONO-15 Locus primer | TCAGATTTATTTTGGGCTTCACTC |
| 46 | MONO-15 Locus primer | GGCGGAGCTTGCAGTGAG |
| 47 | MONO-15 Locus primer | TGTGAACCACCTATGAATTGCAGA |
| 48 | MONO-15 Locus primer | GCTTGCAGTGAGCAGAGATCGTT |
| 49 | D1S518 Locus primer | TGCAGATCTTGGGACTTCTC |
| 50 | D1S518 Locus primer | AAAAAGAGTGTGGGCAACTG |
| 51 | D1S518 Locus primer | GTCAATTCCTTGTTATAAATTATA |

FIG. 6 (continued)

| SEQ ID NO: | Description | SEQUENCE |
|---|---|---|
| 52 | D1S518 Locus primer | ATTGGCAACTGCATTAGAGTTCTC |
| 53 | Human mutator hMSH2 gene exon 5 wild-type form | TGACTACTTTGACTTCAGCCAGTATATGAAATTGGATATTGCAGCAGTCAGAGCCCTAACCTTTTCAGGTAAAAAAAAAAAAAAAAAAGGGTAAAAATGTTGATTGGTTAA |
| 54 | Human mutator hMSH2 gene exon 5 wild-type form | TGACTACTTTGACTTCAGCCAGTATATGAAATTGGATATTGCAGCAGTCAGAGCCCTAACCTTTTCAGGTAAAAAAAAAAAAAAAAAAAGGGTAAAAATGTTGATTGGTTAA |

F = FAM; P = phosphate; U = 5-propynyl dU

FIG. 6 (continued)

```
                          SEQUENCE LISTING

<160> NUMBER OF SEQ ID NOS: 54

<210> SEQ ID NO 1
<211> LENGTH: 33
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (3)..(28)
<223> OTHER INFORMATION: n is 5-propynyl dU

<400> SEQUENCE: 1
ccnnnnnnnn nnnnnnnnnn nnnnnnnnac ctg                                 33

<210> SEQ ID NO 2
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 2
tttttttttt tttttttttt tttttt                                         26

<210> SEQ ID NO 3
<211> LENGTH: 37
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (3)..(32)
<223> OTHER INFORMATION: n is 5-propynyl dU

<400> SEQUENCE: 3
ccnnnnnnnn nnnnnnnnnn nnnnnnnnnn nnacctg                             37

<210> SEQ ID NO 4
<211> LENGTH: 25
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (3)..(20)
<223> OTHER INFORMATION: n is 5-propynyl dU

<400> SEQUENCE: 4
```
ccnnnnnnnn nnnnnnnnnn acctg                                                 25

<210> SEQ ID NO 5
<211> LENGTH: 57
<212> TYPE: DNA
<213> ORGANISM: Artificial
<220> FEATURE:
<223> OTHER INFORMATION: synthetic oligonucleotide probe

<400> SEQUENCE: 5 ttaaccttttt tcaggtaaaa aaaaaaaaaa aaaaaaaaaa aagggttaaa aatgttg           57

<210> SEQ ID NO 6
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 6 taacctttt caggtaaaaa aaaaaaaaaa aaaaaaaggg ttaaaaatgt tg                  52

<210> SEQ ID NO 7
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 7 taacctttt caggtaaaaa aaaaaaaaaa aaagggttaa aaatgttg                      48

<210> SEQ ID NO 8
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 8 taacctttt caggtaaaaa aaaaaaaaag ggttaaaaat gttg                          44

<210> SEQ ID NO 9
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 9 taacctttt caggtaaaaa aaaaagggtt aaaaatgttg                               40

<210> SEQ ID NO 10
<211> LENGTH: 33
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: n is dC 5'-modified with 6-carboxy-fluorescein
      (FAM)
<220> FEATURE:
<221> NAME/KEY: misc_feature
<222> LOCATION: (3)..(28)
<223> OTHER INFORMATION: n is 5-propynyl dU
<220> FEATURE:

```
<221> NAME/KEY: misc_feature
<222> LOCATION: (33)..(33)
<223> OTHER INFORMATION: n is dG 3'-modified with phosphate

<400> SEQUENCE: 10
ncnnnnnnnn nnnnnnnnnn nnnnnnnnac ctn                          33

<210> SEQ ID NO 11
<211> LENGTH: 26
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: n is dT 5'-modified with 6-carboxy-fluorescein
      (FAM)
<220> FEATURE:
<221> NAME/KEY: misc_feature
<222> LOCATION: (26)..(26)
<223> OTHER INFORMATION: n is dT 3'-modified with phosphate

<400> SEQUENCE: 11
nttttttttt tttttttttt tttttn                                  26

<210> SEQ ID NO 12
<211> LENGTH: 37
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: n is dC 5'-modified with 6-carboxy-fluorescein
      (FAM)
<220> FEATURE:
<221> NAME/KEY: misc_feature
<222> LOCATION: (3)..(32)
<223> OTHER INFORMATION: n is 5-propynyl dU
<220> FEATURE:
<221> NAME/KEY: misc_feature
<222> LOCATION: (37)..(37)
<223> OTHER INFORMATION: n is dG 3'-modified with phosphate

<400> SEQUENCE: 12
ncnnnnnnnn nnnnnnnnnn nnnnnnnnnn nnacctn                      37

<210> SEQ ID NO 13
<211> LENGTH: 25
<212> TYPE: DNA
<213> ORGANISM: Artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: n is dC 5'-modified with 6-carboxy-fluorescein
      (FAM)
<220> FEATURE:
<221> NAME/KEY: misc_feature
<222> LOCATION: (3)..(20)
<223> OTHER INFORMATION: n is 5-propynyl dU
<220> FEATURE:
<221> NAME/KEY: misc_feature
<222> LOCATION: (25)..(25)
<223> OTHER INFORMATION: n is dG 3'-modified with phosphate

<400> SEQUENCE: 13
ncnnnnnnnn nnnnnnnnnn acctn                                   25
```

```
<210> SEQ ID NO 14
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 14
taaccttttt caggtaaaaa aaaaaaaaaa aaaagggtta aaaatgttg              49

<210> SEQ ID NO 15
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 15
taaccttttt caggtaaaaa aaaaaaaaaa aaaaagggtt aaaaatgttg             50

<210> SEQ ID NO 16
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 16
taaccttttt caggtaaaaa aaaaaaaaaa aaaaaagggt aaaaatgtt g            51

<210> SEQ ID NO 17
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 17
tcgcctccaa gaatgtaagt                                             20

<210> SEQ ID NO 18
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 18
tctgcatttt aactatggct                                             20

<210> SEQ ID NO 19
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 19
attctgcatt ttaactatgg ctct                                        24

<210> SEQ ID NO 20
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 20
```

-continued tgattccaat catagccaca                    20

<210> SEQ ID NO 21
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 21
cctggaagaa ccaatgctta                    20

<210> SEQ ID NO 22
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 22
ttgagcccag aaagtttgag                    20

<210> SEQ ID NO 23
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 23
aaccaatcaa catttttaac cctt               24

<210> SEQ ID NO 24
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 24
gcttgcagac agcctattgt                    20

<210> SEQ ID NO 25
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 25
gtagagcaag accaccttg                     19

<210> SEQ ID NO 26
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 26
cagaacaaac aaatggggag                    20

<210> SEQ ID NO 27
<211> LENGTH: 20
<212> TYPE: DNA
<213> ORGANISM: Artificial

```
<220> FEATURE:
<223> OTHER INFORMATION: synthetic oligonucleotide primer

<400> SEQUENCE: 27
ccaaataaga ctcaggacgc                                                      20

<210> SEQ ID NO 28
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 28
ggaggaaaag tcttaaacgt gaat                                                 24

<210> SEQ ID NO 29
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 29
attggccttg atgtgtttgt tact                                                 24

<210> SEQ ID NO 30
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 30
ttggtggtgt catcctcttt                                                      20

<210> SEQ ID NO 31
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 31
ctcttaactg atttggccga                                                      20

<210> SEQ ID NO 32
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 32
ccccttggtg gtgtcatcct                                                      20

<210> SEQ ID NO 33
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 33
attgccgatc ctgaagcaat agc                                                  23
```

```
<210> SEQ ID NO 34
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 34
ggcaggcagg tagatagaca                                           20

<210> SEQ ID NO 35
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 35
acactaaaca agcatagtca ggc                                       23

<210> SEQ ID NO 36
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 36
attgtttgca tgtgaaacag gtca                                      24

<210> SEQ ID NO 37
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 37
acatacggat gaatggatgg                                           20

<210> SEQ ID NO 38
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 38
tataacctct ctccctatct ccc                                       23

<210> SEQ ID NO 39
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 39
atttctcata acctctctcc ctatct                                    26

<210> SEQ ID NO 40
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 40
```

-continued atttctctat aacctctctc cctatct                              27

<210> SEQ ID NO 41
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 41
cccccatgag ttattcctct                                      20

<210> SEQ ID NO 42
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 42
ggaagccaaa tgttgaattg                                      20

<210> SEQ ID NO 43
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 43
catttcttct gcccccatga                                      20

<210> SEQ ID NO 44
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 44
atttgacagc tgaaaaggtg cagatg                               26

<210> SEQ ID NO 45
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 45
tcagatttat tttgggcttc actc                                 24

<210> SEQ ID NO 46
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 46
ggcggagctt gcagtgag                                        18

<210> SEQ ID NO 47
<211> LENGTH: 24
<212> TYPE: DNA
<213> ORGANISM: Artificial

```
<220> FEATURE:
<223> OTHER INFORMATION: synthetic oligonucleotide primer

<400> SEQUENCE: 47
tgtgaaccac ctatgaattg caga                                              24

<210> SEQ ID NO 48
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 48
gcttgcagtg agcagagatc gtt                                               23

<210> SEQ ID NO 49
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 49
tgcagatctt gggacttctc                                                   20

<210> SEQ ID NO 50
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 50
aaaaagagtg tgggcaactg                                                   20

<210> SEQ ID NO 51
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 51
gtcaattcct tgttataaaa ttata                                             25

<210> SEQ ID NO 52
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 52
attggcaact gcattagagt tctc                                              24

<210> SEQ ID NO 53
<211> LENGTH: 123
<212> TYPE: DNA
<213> ORGANISM: Homo sapiens

<400> SEQUENCE: 53
tgactacttt tgacttcagc cagtatatga aattggatat tgcagcagtc agagcccta        60 acctttttca ggtaaaaaaa aaaaaaaaa aaaaaaaag ggttaaaaat gttgattggt        120
taa                                                                    123
```

```
<210> SEQ ID NO 54
<211> LENGTH: 119
<212> TYPE: DNA
<213> ORGANISM: Homo sapiens

<400> SEQUENCE: 54
tgactacttt tgacttcagc cagtatatga aattggatat tgcagcagtc agagccctta      60
acctttttca ggtaaaaaaa aaaaaaaaaa aaaagggtt aaaaatgttg attggttaa      119
```

METHOD FOR DETECTING A MUTATION IN A REPETITIVE NUCLEIC ACID SEQUENCE

CROSS-REFERENCE TO RELATED APPLICATIONS

This application claims priority to and benefit of U.S. Provisional Patent Application Ser. No. 60/702,501, filed Jul. 25, 2005, the content of which is hereby incorporated by reference in its entirety.

FIELD OF THE INVENTION

The present invention relates to the detection of target nucleic acids that include repetitive nucleotide sequences. For example, certain aspects of the invention relate to the detection of instability in regions of genomic DNA that include tandem repeats, such as microsatellite markers.

BACKGROUND OF THE INVENTION

Repetitive nucleotide sequences, such as direct or inverted repeats, are observed in many organisms. As an example, hundreds of thousands of microsatellite loci are distributed throughout the human genome and thus, occur statistically about once every 100,000 base pairs. A microsatellite locus is a region of genomic DNA that includes short tandem repeats in which the shortest repetitive units are typically from one to five nucleotides in length. Accordingly, a repetitive unit of a particular microsatellite locus is commonly referred to as a mono-, di-, tri-, tetra- or pentanucleotide repeat locus, as applicable. A given microsatellite locus typically includes between about 10 and 40 of these repetitive units in the tandem arrangement. Further, each microsatellite locus of normal genomic DNA for most diploid species, such as genomic DNA from mammalian species, includes two alleles at each locus. The two alleles can be identical to, or differ from, one another in length and may vary from one individual to the next.

Microsatellite instability (MSI), or replication error (RER), is an example of genomic instability that occurs in certain human neoplasms in which tumor cells have diminished abilities to accurately replicate their DNA. MSI is a common marker of an underlying functional inactivation of a human DNA mismatch repair (MMR) gene (Jeong et al. (2003) "Microsatellite instability and mutations in DNA mismatch repair genes in sporadic colorectal cancers," *Dis Colon Rectum.* 46(8):1069-1077, Papadopoulos et al. (1994) "Mutations of a mutL homolog in hereditary colon cancer," *Science* 263:1625-1629, Ghimenti et al. (1999) "Microsatellite instability and mismatch repair gene inactivation in sporadic pancreatic and colon tumours," *Br J Cancer.* 80(1-2): 11-16, Fishel et al. (1993) "The human mutator gene homolog MSH2 and its association with hereditary nonpolyposis colon cancer," *Cell* 75:1027-1038, and Bronner et al. (1994) "Mutation in the DNA mismatch repair gene homologue hMLH1 is associated with hereditary non-polyposis colon cancer," *Nature* 368:258-261, which are incorporated by reference). The functional loss of a MMR gene is thought to occur due to biallelic inactivation via coding region mutations, loss of heterozygosity (LOH), and/or promoter methylation (Goel et al. (2004) "Frequent inactivation of PTEN by promoter hypermethylation in microsatellite instability-high sporadic colorectal cancers," *Cancer Res.* 64(9):3014-3021, Veigl et al. (1998) "Biallelic inactivation of hMLH1 by epigenetic gene silencing, a novel mechanism causing human MSI cancers," *Proc Natl Acad Sci USA* 95:8698-8702, and Piao et al. (2000) "Frequent frameshift mutations of RIZ in sporadic gastrointestinal and endometrial carcinomas with microsatellite instability," *Cancer Res.* 60, 4701-4704, which are each incorporated by reference). Further, germline mutation of a MMR gene has been shown to be the autosomal dominant genetic defect in most hereditary nonpolyposis colon cancer (HNPCC) kindreds (Eshleman et al. (1995) "Microsatellite instability in inherited and sporadic neoplasms," *Curr Opin Oncol* 7:83-89, which is incorporated by reference). A second mutation incurred by tumor cells in HNPCC individuals results in biallelic inactivation of the specific MMR gene, causing loss of accurate replication of microsatellite DNA in tumors (Hemminki et al. (1994) "Loss of the wild type MLH1 gene is a feature of hereditary non-polyposis colorectal cancer," *Nat Genet* 8:405-410, which is incorporated by reference). MSI is thus a marker of an underlying DNA mismatch repair defect and is also associated with enhanced mutation rates in coding DNA (Eshleman et al. (1995) "Increased mutation rate at the hprt locus accompanies microsatellite instability in colon cancer," *Oncogene* 10:33-37 and Bhattacharyya et al. (1994) "Mutator phenotypes in human colorectal carcinoma cell lines," *Proc Natl Acad Sci USA* 91:6319-6323, which is incorporated by reference). This mutator phenotype, which results from the MMR defect, causes both coding region base substitutions and frameshift mutations at direct repeats, each occurring at equal frequencies (Eshleman et al. (1996) "Diverse hypermutability of multiple expressed sequence motifs present in a cancer with microsatellite instability," *Oncogene* 12:1425-1432, which is incorporated by reference), in addition to resulting in MSI. The generation of MMR defects and the resultant mutator phenotype is thought to be an early event in tumorigenesis (Parsons et al. (1993) "Hypermutability and mismatch repair deficiency in RER+ tumor cells," *Cell* 75(6):1227-1236 and Shibata et al. (1994) "Genomic instability in repeated sequences is an early somatic event in colorectal tumorigenesis that persists after transformation," *Nat Genet* 6:273-281, which are both incorporated by reference) and has been suggested to occur as early as the aberrant crypt focus stage (Augenlicht et al. (1996) "Evidence for genomic instability in human colonic aberrant crypt foci," *Oncogene* 12:1767-1772, which is incorporated by reference).

Although implicating a germline defect in HNPCC families, MSI is also found in about 15 to 20% of sporadic colorectal cancers (Aaltonen et al. (1993) "Clues to the pathogenesis of familial colorectal cancer," *Science* 260:812-816, which is incorporated by reference), where the finding also reflects an overall increase in genomic instability. The finding of MSI defects in tumors has also been associated with a better prognosis in stage-for-stage matched tumors (Thibodeau et al. (1993) "Microsatellite instability in cancer of the proximal colon," *Science* 260:816-819 and Sankila et al. (1996) "Better survival rates in patients with MLH1-associated hereditary colorectal cancer," *Gastroenterology* 110:682-687, which is incorporated by reference). Thus, it is clinically relevant to identify tumors with MSI not only to implicate germline MMR defects (HNPCC families), but also for prognostic stratification. While clinical (Bethesda guidelines (Rodriguez-Bigas et al. (1997) "A National Cancer Institute workshop on hereditary nonpolyposis colorectal cancer syndrome: meeting highlights and Bethesda guidelines," *J Natl Cancer Inst* 89:1758-1762, which is incorporate by reference)) and histopathological features (Kim et al. (1994) "Clinical and pathological characteristics of sporadic colorectal carcinomas with DNA replication errors in microsatellite sequences," *Am J Pathol* 145:148-156, which is incorporate by reference) may raise the suspicion that a colorectal tumor is microsatellite-unstable and perhaps has arisen in an HNPCC family, clinicopathological features are insufficient to diagnose the presence of MSI. Accordingly, molecular testing may be utilized to elucidate the MSI status of a clinically suspicious tumor (Boland et al. (1998) "A National Cancer Institute workshop on microsatellite instability for cancer detection and familial predisposition: development of international criteria for the determination of microsatellite instability in colorectal cancer," *Cancer Res* 58:5248-5257, which is incorporated by reference).

In addition to colorectal tumors, MSI has also been associated with other types of cancer and other genetic disorders. To illustrate, these include among others, pancreatic carcinomas (Han et al. (1993) "Genetic instability in pancreatic cancer and poorly differentiated type of gastric cancer," *Cancer Res.* 53:5087-5089), gastric carcinomas (Pan et al. (2004) "Detection of frameshift mutations of RIZ in gastric cancers with microsatellite instability," *World J Gastroenterol.* 10(18):2719-2722, French et al. (2004) "Allelic imbalance of 8 p indicates poor survival in gastric cancer," *J Mol Diagn.* 6(3):243-252, Rhyu et al. (1994) "Microsatellite instability occurs frequently in human gastric carcinoma," *Oncogene* 9:29-32, and Han et al. (1993), supra), bladder cancer (Gonzalez-Zulueta et al. (1993) "Microsatellite instability in bladder cancer," *Cancer Res.* 53:5620-5623), prostate carcinomas (Schoenberg et al. (1994) "Microsatellite mutation (CAG2418) in the androgen receptor gene in human prostate cancer," *Biochem. Biophys. Res. Commun.* 198:74-80), lung cancers (Merlo et al. (1994) "Frequent microsatellite instability in primary small cell lung cancer," *Cancer Res.* 54:2098-2101 and Shridhar et al. (1994) "Genetic instability of microsatellite sequences in many non-small cell lung carcinomas," *Cancer Res.* 54:2084-2087), uterine carcinomas (Burks et al. (1994) "Microsatellite instability in endometrial carcinoma," *Oncogene* 9:1163-1166 and Miyai et al. (2004) "Loss of heterozygosity analysis in uterine cervical adenocarcinoma," *Gynecol Oncol.* 94(1):115-120) and breast cancer (Yang et al. (2004) "High-resolution 19p13.2-13.3 allelotyping of breast carcinomas demonstrates frequent loss of heterozygosity," *Genes Chromosomes Cancer* 41(3):250-256 and Yee et al. (1994) "Microsatellite instability and loss of heterozygosity in breast cancer," *Cancer Res.* 54:1641-1644). Other exemplary genetic orders thought to be related to microsatellite instability include, e.g., Huntington's disease (HD), dentatorubral and palidoluysian atrophy (DRPLA), spinobulbar and muscular atrophy (SBMA), myotonic dystrophy (DM), fragile X syndrome, FRAXE mental retardation and spinocerebellar ataxias (SCA) (Costa Lima et al. (2004) "Dynamic mutation and human disorders: the spinocerebellar ataxias (review)," *Int J Mol Med.* 13(2):299-302), Bruton X-linked agammaglobulinemia (XLA) (Allen et al. (1994) "Application of carrier testing to genetic counseling for X-linked agammaglobulinemia," *Am J Hum Genet.* 54(1): 25-35), Bloom syndrome (BS) (Foucault et al. (1996) "Stability of microsatellites and minisatellites in Bloom syndrome, a human syndrome of genetic instability," *Mutat Res.* 362(3):227-236 and Kaneko et al. (1996) "Microsatellite instability in B-cell lymphoma originating from Bloom syndrome," *Int J Cancer.* 69(6):480-483), craniofrontonasal syndrome (CFNS) (Feldman et al. (1997) "A novel phenotypic pattern in X-linked inheritance: craniofrontonasal syndrome maps to Xp22," *Hum Mol Genet.* 6(11):1937-1941), and idiopathic pulmonary fibrosis (IPF) (Mori et al. (2001) "Microsatellite instability in transforming growth factor-beta 1 type II receptor gene in alveolar lining epithelial cells of idiopathic pulmonary fibrosis," *Am J Respir Cell Mol Biol.* 24(4):398-404). All of the publications mentioned in this paragraph are incorporated by reference.

In view of the foregoing discussion, it is apparent that the analysis of repetitive nucleotide sequences, such as microsatellites has many diagnostic and prognostic applications among other uses. Among the limitations of pre-existing microsatellite analytical methodologies is the lack of rapid assays that can be performed in the order of minutes. For example, certain pre-existing MSI detection methods include amplifying microsatellite loci of interest by polymerase chain reaction (PCR), performing minisequencing reactions, and analyzing the products via gel electrophoresis. These complex, labor-intensive processes are not well suited to providing rapid results.

SUMMARY OF THE INVENTION

The present invention provides approaches for rapidly and reliably detecting and differentiating between mutant and non-mutant forms of nucleic acids that comprise repetitive nucleotide sequences. In certain embodiments, for example, the methods described herein are used to assess microsatellite instability in patients as part of diagnostic or prognostic applications. In many embodiments, various polymorphisms of a given repetitive nucleotide sequence are detected using a single probe nucleic acid. In addition to methods and probes, the invention also provides related reaction mixtures, kits, and systems.

In one aspect, the invention provides a method of detecting a mutant form of a target nucleic acid. The method includes providing at least one target nucleic acid and/or an amplicon of the target nucleic acid. The target nucleic acid includes at least one repetitive nucleotide sequence. The method also includes binding (e.g., hybridizing, etc.) at least one probe nucleic acid to the target nucleic acid and/or to the amplicon of the target nucleic acid. The probe nucleic acid includes at least a first nucleotide sequence that is at least substantially complementary to at least a portion of a non-mutant form of the repetitive nucleotide sequence. In addition, the method also includes detecting a bimodal dissociation of the probe nucleic acid from the target nucleic acid and/or from the amplicon of the target nucleic acid. In some embodiments, the detected bimodal dissociation comprises a bimodal distribution of melting peaks. Further, the detected bimodal dissociation generally correlates with at least one mutant form of the repetitive nucleotide sequence. In some embodiments, a detected non-bimodal (e.g., a single mode, etc.) dissociation correlates with a non-mutant form the repetitive nucleotide sequence. Typically, the probe nucleic acid, the target nucleic acid, and/or the amplicon of the target nucleic acid includes or is associated with at least one labeling moiety and/or at least one quencher moiety. In these embodiments, the detecting step generally includes detecting a detectable signal produced by the labeling moiety. Moreover, the bimodal dissociation of the probe nucleic acid from the target nucleic acid and/or from the amplicon of the target nucleic acid is typically detected under at least one varied condition, such as a varied temperature or the like.

In another aspect, the invention provides a reaction mixture. The reaction mixture includes at least one target nucleic acid and/or an amplicon of the target nucleic acid. The target nucleic acid includes at least one repetitive nucleotide sequence. The reaction mixture also includes at least one probe nucleic acid that includes at least a first nucleotide sequence that is at least substantially complementary to at least a portion of a non-mutant form of the repetitive nucleotide sequence. Further, the probe nucleic acid dissociates bimodally from a bound target nucleic acid that includes at least one mutant form of the repetitive nucleotide sequence under at least one varied condition.

In certain embodiments, the reaction mixture of the invention also includes various other components. For example, the reaction mixture optionally includes at least one salt (e.g., NaCl, KCl, and/or the like). In some embodiments, the reaction mixture also includes at least one buffer. The buffer typically maintains a pH of the reaction mixture between about 5.5 and about 10.0. The reaction mixture also optionally includes at least one cofactor, such as $Mg^{2+}$ (e.g., $MgSO_4$, $MgCl_2$, etc.), $Mn^{2+}$ (e.g., $MnSO_4$, $MnCl_2$, etc.), and/or the like.

In still another aspect, the invention provides a probe nucleic acid. The probe nucleic acid includes at least a first nucleotide sequence that is at least substantially complementary to at least a portion of a non-mutant form of a repetitive nucleotide sequence. In addition, the probe nucleic acid dissociates bimodally from a bound target nucleic acid that includes at least one mutant form of the repetitive nucleotide sequence under at least one varied condition.

In another aspect, the invention provides a kit that includes at least one probe nucleic acid that comprises at least a first nucleotide sequence that is at least substantially complementary to at least a portion of a non-mutant form of a repetitive nucleotide sequence. The probe nucleic acid dissociates bimodally from a bound polynucleotide that includes at least one mutant form of the repetitive nucleotide sequence under at least one varied condition. Typically, the probe nucleic acid is provided in solution. The kit also includes instructions for detecting dissociation of the probe nucleic acid from a bound target nucleic acid and/or from a bound amplicon of the target nucleic acid that includes the repetitive nucleotide sequence. In some embodiments, the kit also includes instructions for one or more of, e.g., obtaining the target nucleic acid from a subject, amplifying at least a portion of the target nucleic acid, binding the probe nucleic acid to the target nucleic acid and/or the amplicon of the target nucleic acid, varying at least one condition, correlating a detected bimodal dissociation with a diagnosis of at least one genetic disorder and/or at least one disease state for a subject, or the like. In addition, the kit optionally also includes one or more components selected from, e.g., at least one nucleotide incorporating biocatalyst, at least one nucleotide, at least one pyrophosphatase, at least one uracil N-glycosylase, at least one salt, at least one buffer, at least one cofactor, and the like. Typically, the kit also includes at least one container for packaging the probe nucleic acid, the instructions, and/or one or more other components.

In still another aspect, the invention provides a system for detecting mutant forms of target nucleic acids. The system includes at least one probe nucleic acid that includes at least a first nucleotide sequence that is at least substantially complementary to a non-mutant form of a repetitive nucleotide sequence. The probe nucleic acid dissociates bimodally from a bound target nucleic acid that comprises at least one mutant form of the repetitive nucleotide sequence under at least one varied condition. Typically, at least one container comprises the probe nucleic acid, e.g., in solution. The system also includes at least one detector that detects dissociation of the probe nucleic acid from a target nucleic acid and/or from an amplicon of the target nucleic acid when the probe nucleic acid is bound to the target nucleic acid and/or to the amplicon of the target nucleic acid and subjected to one or more varied conditions. In some embodiments, the system also includes at least one thermal modulator that modulates temperatures to which the probe nucleic acid is exposed when the probe nucleic acid is bound to the target nucleic acid and/or to the amplicon of the target nucleic acid to effect the varied conditions. In certain embodiments, the system also includes at least one controller operably connected at least to the detector, which controller correlates detected bimodal dissociations of the probe nucleic acid from bound target nucleic acids and/or bound amplicons of target nucleic acids with diagnoses of at least one genetic disorder and/or at least one disease state for subjects from which the target nucleic acids were obtained.

The target nucleic acid used in the methods, reaction mixtures, kits, systems, and other aspects of the invention include various embodiments. To illustrate, the target nucleic acid typically comprises a DNA or an RNA, and is generally obtained from at least one subject. Mutant forms of the target nucleic acid typically correlate with a diagnosis of at least one genetic disorder (e.g., Fragile X Syndrome, etc.) and/or at least one disease state (e.g., at least one form of cancer, etc.) for a subject comprising the mutant form of the target nucleic acid. Further, the mutant form of the repetitive nucleotide sequence typically comprises at least one deletion relative to the non-mutant form of the repetitive nucleotide sequence. In some embodiments, for example, the repetitive nucleotide sequence corresponds to a microsatellite marker, a mononucleotide repeat, and/or the like. In some embodiments, the repetitive nucleotide sequence comprises at least one mononucleotide repeat (e.g., $A_n$, $T_n$, $G_n$, $C_n$, $U_n$, etc., where n is an integer greater than 1). For example, the mononucleotide repeat optionally comprises a BAT-25 repeat, a BAT-26 repeat, among many others. In certain embodiments, detected mutant forms of the mononucleotide repeat comprise 22 or fewer adenine nucleotides. To further illustrate, the repetitive nucleotide sequence of the target nucleic acid includes at least one AT repeat, at least one GC repeat, at least one CGG repeat, at least one CGC repeat, at least one TAT repeat, at least one ATT repeat, and/or at least one complementary repeat thereof in certain embodiments.

The probe nucleic acids utilized in the various aspects of the invention also include different embodiments. In some embodiments, for example, the first nucleotide sequence is longer than the non-mutant form of the repetitive nucleotide sequence. In these embodiments, the portion of the first nucleotide sequence that extends beyond the length of the non-mutant form of the repetitive nucleotide sequence is typically not substantially complementary to nucleotide sequences of the target nucleic acid that are adjacent to the repetitive nucleotide sequence. While not being constrained to a particular theory, in these embodiments it is thought that at least one segment of the probe nucleic acid forms a triple helix when the probe nucleic acid is bound to the mutant form of the target nucleic acid or to an amplicon of the mutant form of the target nucleic acid under at least one selected condition. In certain embodiments, the probe nucleic acid comprises at least one modified nucleotide. In certain embodiments, the probe nucleic acid includes a sequence selected from the group consisting of: SEQ ID NOS: 1-4 and complements thereof. Optionally, a solid support comprises the probe nucleic acid.

The probe nucleic acids, target nucleic acids, and/or amplicons of the target nucleic acids (e.g., via primer nucleic acids used to produce the amplicons, etc.) optionally comprise or are associated with at least one labeling moiety and/or at least one quencher moiety. To illustrate, the labeling moiety optionally comprises one or more of, e.g., a fluorescent dye, a weakly fluorescent label, a non-fluorescent label, a colorimetric label, a chemiluminescent label, a bioluminescent label, an antibody, an antigen, biotin, a hapten, an enzyme, or the like. To further exemplify, the fluorescent dye is optionally selected from the group consisting of, e.g., Cy3, Cy3.5, Cy5, Cy5.5, JOE, VIC, TET, HEX, FAM, R6G, R110, TAMRA, ROX, SYBR-Green, EtBr, and the like.

BRIEF DESCRIPTION OF THE DRAWINGS

FIG. 6 provides nucleotide sequences finding use with the invention.

DETAILED DESCRIPTION

I. Definitions

Figure 1:
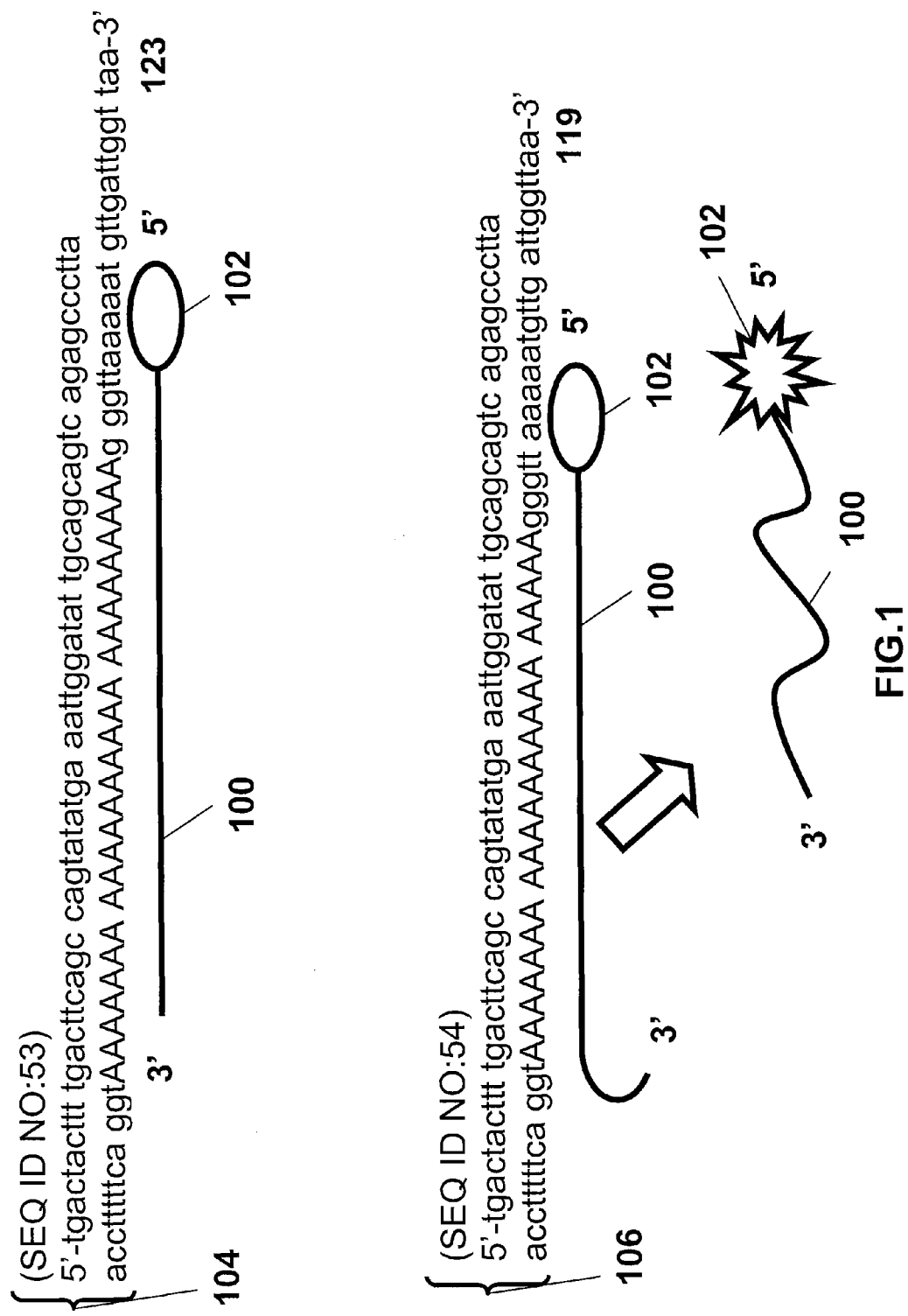
FIG. 1 schematically illustrates an assay in which a probe nucleic acid differentially dissociates from target nucleic acids having mutant or non-mutant forms of BAT-26.

Before describing the present invention in detail, it is to be understood that this invention is not limited to particular embodiments. It is also to be understood that the terminology used herein is for the purpose of describing particular embodiments only, and is not intended to be limiting. Units, prefixes, and symbols are denoted in the forms suggested by the International System of Units (SI), unless specified otherwise. Numeric ranges are inclusive of the numbers defining the range. As used in this specification and the appended claims, the singular forms "a", "an" and "the" also include plural referents unless the context clearly dictates otherwise. Thus, for example, reference to "a target nucleic acid" also includes multiple target nucleic acids, which are simultaneously detected in certain multiplexing embodiments of the methods described herein. Further, unless defined otherwise, all technical and scientific terms used herein have the same meaning as commonly understood by one of ordinary skill in the art to which the invention pertains. The terms defined below, and grammatical variants thereof, are more fully defined by reference to the specification in its entirety.

An "amplicon" refers to a molecule made by copying or transcribing another molecule. Exemplary processes in which amplicons can be produced include transcription, cloning, and/or a polymerase chain reaction ("PCR") or another nucleic acid amplification technique (e.g., strand displacement PCR amplification (SDA), duplex PCR amplification, etc.). Typically, an amplicon is a copy of a selected nucleic acid (e.g., a template or target nucleic acid) or is complementary thereto.

The term "amplify" refers to a process in which multiple copies are made of one or more nucleic acid loci. Amplification can be accomplished using essentially any nucleic acid amplification technique, including but not limited to the polymerase chain reaction (PCR) (Saiki et al. (1985) "Enzymatic amplification of beta-globin genomic sequences and restriction site analyses for diagnosis of sickle cell anemia," *Science* 230:1350-1354), reverse-transcription PCR (RT-PCR) (Joyce (2002) "Quantitative RT-PCR. A review of current methodologies" *Methods Mol Biol.* 193:83-92 and Emrich et al. (2002) "Quantitative detection of telomerase components by real-time, online RT-PCR analysis with the LightCycler," *Methods Mol Biol.* 191:99-108), the ligase chain reaction (LCR) (Lee (1996) "Ligase chain reaction," *Biologicals* 24(3):197-9), the polymerase ligase chain reaction (Barany et al. (1991) "The ligase chain reaction in a PCR world," *PCR Methods Appl.* 1(1):5-16), the Gap-LCR (Abravaya et al. (1995) "Detection of point mutations with a modified ligase chain reaction (Gap-LCR)," *Nucleic Acids Res.* 23(4):675-82), strand displacement amplification (SDA) (Walker (1993) "Empirical aspects of strand displacement amplification," *PCR Methods Appl.* 3(1):1-6), linked linear amplification (LLA) (Killeen et al. (2003) "Linked linear amplification for simultaneous analysis of the two most common hemochromatosis mutations," *Clin Chem.* 49(7): 1050-7), rolling circle amplification (RCA) (Nilsson et al. (2002) "Real-time monitoring of rolling-circle amplification using a modified molecular beacon design," *Nucleic Acids Res.* 30(14):e66), transcription-mediated amplification (TMA) (Emery et al. (2000) "Evaluation of performance of the Gen-Probe human immunodeficiency virus type 1 viral load assay using primary subtype A, C, and D isolates from Kenya," *J Clin Microbiol* 38:2688-2695), nucleic-acid-sequence-based amplification (NASBA) (Mani et al. (1999) "Plasma RNA viral load as measured by the branched DNA and nucleic acid sequence-based amplification assays of HIV-1," *J Acquir Immune Defic Syndr* 22:208-209 and Berndt et al. (2000) "Comparison between a nucleic acid sequence-based amplification and branched DNA test for quantifying HIV RNA load in blood plasma," *J Virol Methods* 89:177-181), and self-sustaining sequence replication (3SR) (Mueller et al. (1997) "Self-sustained sequence replication (3SR): an alternative to PCR," *Histochem Cell Biol* 108:431-7). All of the references cited in this paragraph are incorporated by reference.

A "BAT-25 repeat" and a "BAT-26 repeat" are mononucleotide microsatellites. They are thought to have a quasi-monomorphic allele length distribution in healthy subject but unstable, shortened alleles in solid organ tumors with mutator phenotypes (e.g., RER+). Both markers are highly sensitive and specific for RER+ colorectal cancer (Faulkner et al. (2004) "BAT-25 and BAT-26, two mononucleotide microsatellites, are not sensitive markers of microsatellite instability in acute myeloid leukaemia," *Br J Haematol.* 124(2):160-165, which is incorporated by reference).

A "bimodal dissociation" in the context of nucleic acids refers to a process in which two or more bound nucleic acids separate from each other in two modes, steps, or stages. In certain embodiments, for example, probes dissociates in two steps from bound target nucleic acids under selected conditions. A "non-bimodal dissociation" in the context of nucleic acids refers to a process in which two or more bound nucleic acids separate from one another in other than two modes, steps, or stages, such as in a single mode, step, or stage, etc.

A "bimodal distribution of melting peaks" in the context of a nucleic acid melting point analysis refers to a detectable signal trace having two distinguishable peaks that is detected for the dissociation of nucleic acids from one another over a range of temperatures.

The term "buffer" refers to a substance or mixture of substances that is resistant to changes in pH. Illustrative buffers include tris-(hydroxymethyl)aminoethane (TRIS), tris-(hydroxymethyl)aminomethane sodium phosphate, sodium acetate, sodium citrate, and the like.

A "cofactor" refers to a substance that facilitates a desired effect or that acts with one or more other substances to bring about certain effects. In certain reaction mixtures described herein, for example, metal ions, such as $Mg^{2+}$, $Mn^{2+}$, etc. are used to facilitate the detection of mutant forms of target nucleic acids.

A "complement" of a nucleic acid refers to at least a nucleic acid segment that can combine (e.g., hybridize in accordance with the Watson-Crick-type base-pairing rules, Hoogsteen-type base-pairing rules, etc.) with at least a subsequence of that nucleic acid (e.g., in an antiparallel association, etc.). The association can be intramolecular, e.g., in the form of a hairpin loop within a nucleic acid, or intermolecular, such as when two or more single-stranded nucleic acids hydridize with one another. To illustrate, the sequence 5'-AGTTC-3' is complementary to the sequence 5'-GAACT-3'. Certain bases not commonly found in natural nucleic acids may be included in complementary nucleic acids. Examples of these include, inosine and 7-deazaguanine, among many others referred to herein or otherwise known to those skilled in the art. The term "completely complementary" or "100% complementary" and the like refer to complementary sequences or regions of a sequence that has perfect or exact pairing of bases between the strands or regions of the sequence (i.e., no mismatches in the complements). However, complementarity need not be perfect (i.e., nucleic acids can be "partially complementary" or "substantially complementary"); stable duplexes, for example, may contain mismatched base pairs or unmatched bases. The term "partially complementary" refers to complementary sequences or regions of a sequence that has one or more mismatching base pairs (e.g., due to deletions, insertions, and/or substitutions) between the strands or regions of the sequence. Further, the term "substantially complementary" refers to complementary sequences or regions of a sequence in which about 80% or more (e.g., 85%, 90%, 95%, 100%, or any value therebetween) of the nucleotides have perfect or exact pairing of bases between the strands or regions of the sequence, e.g., when the strands or regions of the sequence are aligned for maximal exact base pairing. Those skilled in the art of nucleic acid technology can determine, e.g., duplex or triplex stability by empirically considering a number of variables including, for example, the length of a region of complementarity, base composition and sequence of nucleotides in a region of complementarity, ionic strength, and incidence of mismatched base pairs. The term "complement thereof" refers to a nucleic acid that is both the same length as, and exactly complementary to, a given nucleic acid.

A "controller" refers an object or device that controls or otherwise effects the intended operation of one or more components of a system. In some embodiments, for example, a controller includes a computer or other logic device.

The term "correlate" means to show a relationship between two or more variables. In certain embodiments, for example, a detected bimodal dissociation of a probe from a target nucleic acid having a repetitive nucleotide sequence correlates with at least one mutant form of the repetitive nucleotide sequence.

The term "deletion" in the context of a nucleic acid sequence refers to an alteration in which at least one nucleotide is removed from the nucleic acid sequence, e.g., from a 5'-terminus, from a 3'-terminus, and/or from an internal position of the nucleic acid sequence.

A "diagnosis" refers to the act of identifying a disease state or a genetic disorder of a subject. In some embodiments, for example, disease states and genetic disorders are diagnosed when mutant forms of target nucleic acids from subjects are detected.

A "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

A "genetic disorder" or "disease state" refers to a condition caused by or that otherwise correlates with one or more mutations in a gene or a set of genes. General categories of genetic disorders include chromosome disorders, single-gene disorders, multifactorial disorders, and mitochondrial disorders. A genetic disorder or disease state may impair the normal functioning of a living organism's body, or component part thereof, or indicate a predisposition or susceptibility to such an impairment. Exemplary genetic disorders or disease states include various types of carcinoma, Huntington's disease (HD), dentatorubral and palidoluysian atrophy (DRPLA), spinobulbar and muscular atrophy (SBMA), myotonic dystrophy (DM), fragile X syndrome, FRAXE mental retardation and spinocerebellar ataxias (SCA), Bloom syndrome (BS), craniofrontonasal syndrome (CFNS), idiopathic pulmonary fibrosis (IPF), and the like.

Nucleic acids "hybridize" or "bind" when they associate with one another, typically in solution. Nucleic acids hybridize due to a variety of well characterized physico-chemical forces, such as hydrogen bonding, solvent exclusion, base stacking and the like. Hybridization can occur between fully complementary nucleic acid strands or between partially complementary nucleic acid strands that include regions of mismatch. The degree of mismatch tolerated can generally be controlled by suitable adjustment of the hybridization conditions. Further, those skilled in the art of nucleic acid chemistry and molecular biology can determine duplex stability empirically by considering a number of variables including, e.g., the length and base pair concentration of the nucleic acids, ionic strength, and incidence of mismatched base pairs. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel (Ed.) *Current Protocols in Molecular Biology*, Volumes I, II, and III, (1997), which are each incorporated by reference. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides. Both Hames and Higgins 1 and 2 are incorporated by reference.

The phrase "in solution" refers to an assay or reaction condition in which the components of the assay or reaction are not attached to a solid support and are present in a liquid medium. Exemplary liquid mediums include aqueous and organic fluids. For example, certain assays of the invention include incubating probes together with target nucleic acid amplicons in solution to allow hybridization to occur.

A "label" or "labeling moiety" refers to a moiety attached (covalently or non-covalently), or capable of being attached or associated, to or with a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg., USA). Dyes of the cyanine family include, e.g., Cy2, Cy3, Cy3.5, Cy5, Cy5.5, and Cy7, and are commercially available from, e.g., Amersham Biosciences Corp. (Piscataway, N.J., USA). DNA binding dyes include, e.g., SYBR-Green, which is commercially available from, e.g., Molecular Probes, Inc. (Eugene, Oreg., USA) and EtBr, which is commercially available from, e.g., Sigma-Aldrich Corp. (St. Louis, Mo., USA).

A "microsatellite marker" or "microsatellite locus" refers to a region of genomic DNA that includes nucleotide repeats. These repeats or "repetitive units" are typically from about one to about seven base pairs in length. Microsatellite loci typically include between about 10 and about 40 of these repetitive units in a tandem arrangement.

A "mixture" refers to a combination of two or more different components. A "reaction mixture" refers a mixture that comprises molecules that can participate in and/or facilitate a given reaction. To illustrate, an amplification reaction mixture generally includes a solution containing reagents necessary to carry out an amplification reaction, and typically contains primers, a nucleic acid polymerase or other nucleotide incorporating biocatalyst, dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components.

A "modified nucleotide" refers to a nucleotide that comprises one or more non-naturally occurring moieties. In some embodiments, for example, modified nucleotides include non-naturally occurring bases and/or sugar moieties. Typically, a modified nucleotide provides a desired property to a nucleic acid (e.g., an oligonucleotide, etc.) that comprises the modified nucleotide. In certain embodiments, modified nucleotides modify melting temperatures ($T_m$) of these oligonucleotides relative to the melting temperatures of corresponding unmodified oligonucleotides. To further illustrate, certain modified nucleotides can reduce non-specific nucleic acid amplification (e.g., minimize primer dimer formation, etc.), increase the yield of an intended target amplicon, and/or the like in some embodiments of the invention. Examples of these types of nucleic acid modifications are described in, e.g., U.S. Pat. No. 6,001,611, entitled "MODIFIED NUCLEIC ACID AMPLIFICATION PRIMERS," issued Dec. 14, 1999 to Will, which is incorporated by reference. Exemplary modified nucleotides that can be substituted in the oligonucleotides described herein include, e.g., a C5-methyl-dC, a C5-ethyl-dC, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art.

A "mononucleotide repeat" refers to a repeat in which each nucleotide in the repeat comprises the same base. For example, some mononucleotide repeats have sequences selected from, $A_n$, $T_n$, $G_n$, $C_n$, or $U_n$, where n is an integer greater than 1.

A "mutant form" of a nucleic acid has an altered nucleotide sequence relative a non-mutant or wild-type form of the nucleic acid. Exemplary alterations that can produce a mutant form of a nucleic acid include nucleotide substitutions, deletions, and/or insertions.

A "non-mutant form" of a nucleic acid has a nucleotide sequence that predominates in a natural population of organisms or strain of organisms.

The term "nucleic acid" refers to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™s), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, the product of a polymerase chain reaction (PCR) or other nucleic acid amplification reaction, an oligonucleotide, a probe, etc. A nucleic acid can be e.g., single-stranded or double-stranded. Unless otherwise indicated, a particular nucleic acid sequence optionally comprises or encodes complementary sequences, in addition to any sequence explicitly indicated.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10): 1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphophoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) *Chem. Soc. Rev. pp* 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside. In some embodiments, for example, a nucleotide is a phosphate ester of a nucleoside. To illustrate, a nucleotide can include 1, 2, 3, or more phosphate groups covalently linked to a 5' position of a sugar moiety of the nucleoside.

A "nucleotide incorporating biocatalyst" catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes").

The term "operably connected" in the context of system components refers the ability of system components to communicate with one another such that those components are able to perform their intended functions within the system.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition. A hybridization assay carried out using the probe under sufficiently stringent hybridization conditions permits the selective detection of a specific target sequence, such as a mutant form of a nucleic acid. The term "hybridizing region" refers to that region of a nucleic acid that is exactly or substantially complementary to, and therefore hybridizes to, the target sequence. For use in a hybridization assay for the discrimination of one or more nucleotide differences in sequence between mutant and non-mutant forms of a target nucleic acid, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like. In certain embodiments, a probe of the invention is included in a nucleic acid that comprises one or more labels (e.g., a reporter dye, a quencher moiety, etc.), such as a 5'-nuclease probe, a FRET probe, a molecular beacon, or the like, which can be utilized to detect dissociation of the probe from target nucleic acids in a sample. In some embodiments, the hybridizing region of the probe is completely complementary to the target sequence. However, in general, complete complementarity is not necessary (i.e., nucleic acids can be partially complementary to one another); stable duplexes may contain mismatched bases or unmatched bases. Modification of the stringency conditions may be necessary to permit a stable hybridization duplex with one or more base pair mismatches or unmatched bases. Sambrook et al., *Molecular Cloning: A Laboratory Manual*, 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

A "pyrophosphatase" is an enzyme (EC:3.6.1.1) that hydrolyzes pyrophosphate (PPi), which is formed as a product of the many biosynthetic reactions that utilize ATP. In some embodiments of the invention, for example, pyrophosphatase is included in reaction mixtures to minimize pyrophosphorolysis. The activity of pyrophosphatase is typically enhanced by the presence of divalent metal cations, such as magnesium.

A "quencher moiety" or "quencher" refers to a moiety that reduces and/or is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Certain quenchers may re-emit the energy absorbed from, e.g., a fluorescent dye in a signal characteristic for that quencher and thus a quencher can also be a "label." This phenomenon is generally known as fluorescent resonance energy transfer or FRET. Alternatively, a quencher may dissipate the energy absorbed from a fluorescent dye in a form other than light, e.g., as heat. Molecules commonly used in FRET include, for example, fluorescein, FAM, JOE, rhodamine, R6G, TAMRA, ROX, DABCYL, and EDANS. Whether a fluorescent dye is a label or a quencher is defined by its excitation and emission spectra, and the fluorescent dye with which it is paired. For example, FAM is most efficiently excited by light with a wavelength of 488 nm, and emits light with a spectrum of 500 to 650 nm, and an emission maximum of 525 nm. FAM is a suitable donor label for use with, e.g., TAMRA as a quencher, which has at its excitation maximum 514 nm. Exemplary non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, wherein at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Exemplary quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

A "repetitive nucleotide sequence" refers to a sequence of nucleotides (e.g., a repetitive unit) that recurs one or more times in a given nucleic acid. Typically, these repetitive units recur in tandem (e.g., directly or inverted). In addition to mononucleotide repeats, other exemplary repetitive nucleotide sequences include AT repeats, GC repeats, CGG repeats, CGC repeats, TAT repeats, ATT repeats, and/or complementary repeats thereof.

A "salt" is a compound that contains a cation other than $H^+$ and an anion other than hydroxide ion, $OH^-$, or oxide ion, $O^{2-}$.

A "solid support" refers to a solid material that can be derivatized with, or otherwise attached to, a chemical moiety, such as an oligonucleotide probe or the like. Exemplary solid supports include plates, beads, microbeads, tubes, fibers, whiskers, combs, hybridization chips (including microarray substrates, such as those used in GeneChip® probe arrays (Affymetrix, Inc., Santa Clara, Calif., USA) and the like), membranes, single crystals, ceramic layers, self-assembling monolayers, and the like.

A "sequence" of a nucleic acid refers to the order and identity of nucleotides in the nucleic acid. A sequence is typically read in the 5' to 3' direction.

A "subject" refers to an organism. Typically, the organism is a mammalian organism, particularly a human organism. In certain embodiments, for example, a subject is a patient suspected of having microsatellite instability at one or more loci.

A "system" refers a group of objects and/or devices that form a network for performing a desired objective. In some embodiments, for example, a system of the invention includes probe nucleic acids, thermal modulators, controllers, and detectors that together are utilized to detect mutant forms of target nucleic acids (e.g., instability in microsatellite markers).

The term "template nucleic acid" or "target nucleic acid" refers to a nucleic acid that is to be amplified, detected, or otherwise analyzed.

A "thermal modulator" refers to a device or instrument that selectively modulates the temperature of one or more objects that are in thermal communication with the modulator. In some embodiments, thermal modulators a thermocycling devices that are utilized to systematically vary temperatures in reaction mixtures as part of nucleic acid melting point analyses.

A "triple helix" in the context of nucleic acids refers to a complex that includes duplex DNA bases that make specific hydrogen-bond contacts with substituents on a third strand of bases. Triple helices can include inter- and/or intra-molecular binding interactions.

A "uracil N-glycosylase" is an enzyme that hydrolyses the release of free uracil from uracil-containing DNA (single- or double-stranded).

II. Introduction

The present invention relates to high-throughput techniques for detecting and distinguishing between mutant and non-mutant forms of nucleic acids that include repetitive nucleotide sequences. In certain applications of these techniques, mutant forms of such target nucleic acids correlate with genetic disorders and accordingly, upon detection provide diagnostic and/or prognostic information about subjects from which the target nucleic acids were obtained. In some aspects, for example, the invention provides for the detection of microsatellite instability in processes that include target nucleic acid amplification and probe nucleic acid melting point analyses. These detection methodologies are typically more rapid and less labor intensive than many pre-existing approaches, such as those based on microsatellite minisequencing.

To further illustrate certain aspects of the invention, various polymorphisms of a given repetitive nucleotide sequence are generally detected using a single probe nucleic acid. In these embodiments, probe nucleic acids are typically longer than non-mutant forms of targeted repetitive nucleotide sequences and dissociate differentially from these non-mutant forms than from mutant forms, such as those having deletions. To illustrate, FIG. 1 schematically depicts probe 100 bound to target nucleic acids 104 and 106. Probe 100 includes fluorescent label 102 (e.g., FAM, etc.) at a 5'-end of the molecule. Label 102 is quenched when probe 100 is bound to nucleic acids. Fluorescence from label 102 detectably increases when probe 100 dissociates from nucleic acids. Target nucleic acids 104 and 106 are shown as a subsequence of exon 5 of the human mutator hMSH2 gene that includes the microsatellite marker BAT-26. Target nucleic acid 104 includes the non-mutant or wild-type form (26 deoxyadenosine nucleotides or $(dA)_{26}$) of BAT-26, while target nucleic acid 106 includes a mutant form ($(dA)_{22}$) of BAT-26. As shown, probe 100 is longer than the mutant form of BAT-26 of target nucleic acid 106. Accordingly, probe 100 dissociates or "melts off" of target nucleic acid 106 at a lower temperature than probe 100 dissociates from target nucleic acid 104 due to shorter base pairing. As a consequence, a detectable increase in fluorescence from label 102 is observed when probe 100 dissociates from target nucleic acid 106 at the lower temperature.

Among the surprising aspects of the invention is that the probe nucleic acids described herein typically dissociate bimodally from mutant forms of repetitive nucleotide sequences, but with single modes from non-mutant forms of the repetitive nucleotide sequences. When probe melting point analyses are used to detect the dissociation of probe nucleic acids from target nucleic acids, bimodal dissociations typically comprise a bimodal distribution of melting peaks for the nucleic acids. While not being constrained to a particular theory of operation, it is thought that at least one segment of a probe nucleic acid described herein forms a triple helix with the target nucleic acid when the probe is bound to a mutant form of a repetitive nucleotide sequence of the target nucleic acid under selected conditions (e.g., a temperature condition, etc.). In contrast, when the same probe is bound to a non-mutant form of the repetitive nucleotide sequence of the target nucleic acid, it is thought that the probe does not form such a triple helix under those selected conditions. This triple helix formation may account for the observed bimodal or two stage dissociation of the probe from the mutant form of the repetitive nucleotide sequence. In any event, this differential dissociation can be used to detect and distinguish between mutant and non-mutant forms of a repetitive nucleotide sequence of a target nucleic acid using a single probe nucleic acid. This differential dissociation is also illustrated in the examples provided below.

In practicing the present invention, many conventional techniques in molecular biology and recombinant DNA are optionally used. These techniques are well known and are explained in, for example, *Current Protocols in Molecular Biology*, Volumes I, II, and III, 1997 (F. M. Ausubel ed.); Sambrook et al., *Molecular Cloning: A Laboratory Manual*, 3rd Ed., Cold Spring Harbor Laboratory Press, Cold Spring Harbor, N.Y., 2001; Berger and Kimmel, *Guide to Molecular Cloning Techniques, Methods in Enzymology* volume 152 Academic Press, Inc., San Diego, Calif. (Berger); *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively), all of which are incorporated by reference.

In addition to methods and probes for detecting mutant forms of target nucleic acids, the present invention also provides related reaction mixtures, kits, and systems, which are described further below.

III. Target Nucleic Acids

Essentially any nucleic acid that includes a repetitive nucleotide sequence can be targeted using the probes and methods described herein. As a consequence, no attempt is made herein to mention all of the possible target nucleic acids. To illustrate, however, in certain embodiments mutant forms of a target nucleic acid (e.g., a DNA or an RNA) correlate with a diagnosis of a genetic disorder or disease state for a subject having the mutant form of the target nucleic acid. Typically, mutant forms of repetitive nucleotide sequences comprise at least one deletion relative to non-mutant forms of the repetitive nucleotide sequences. Exemplary disease states or genetic orders thought to be related to microsatellite instability include, e.g., various types of cancer (including, e.g., certain types of colorectal cancers (e.g., HNPCC, etc.), pancreatic carcinomas, gastric carcinomas, bladder cancers, prostate carcinomas, lung cancers, uterine carcinomas, breast cancers, etc.), Huntington's disease (HD), dentatorubral and palidoluysian atrophy (DRPLA), spinobulbar and muscular atrophy (SBMA), myotonic dystrophy (DM), fragile X syndrome, FRAXE mental retardation and spinocerebellar ataxias (SCA), Bruton X-linked agammaglobulinemia (XLA), Bloom syndrome (BS), craniofrontonasal syndrome (CFNS), and idiopathic pulmonary fibrosis (IPF). Microsatellite markers associated with any of these disease states or genetic orders, among many others, are optionally assessed using the probes and methods described herein. Optionally, the stability of multiple microsatellite loci is assessed simultaneously in certain multiplexing embodiments. In some embodiments, for example, the methods described herein can be used to classify tumors as having, e.g., a high frequency of MSI (MSH-H), a low frequency of MSI (MSI-L), or microsatellite stable (MSS) (Boland et al. (1998) "A National Cancer Institute Workshop on Microsatellite Instability for cancer detection and familial predisposition: development of international criteria for the determination of microsatellite instability in colorectal cancer," *Cancer Res* 58: 5248-5257).

To further illustrate, a list of some examples of genes with length polymorphisms or microsatellite instability that are associated with genetic orders are provided in Table I. Genes with repeat sequences associated with tumor formation or other diseases are also described in, e.g., Duval et al. (2002) "Mutations at Coding Repeat Sequences in Mismatch Repair-deficient Human Cancers: Toward a New Concept of Target Genes for Instability," *Cancer Research* 62:2447-2454, Houlston et al. (2001) "Polymorphisms and Colorectal Tumor Risk," *Gastroenterology* 121:282-301, Olipitz et al. (2002) "Defective DNA-mismatch repair: a potential mediator of leukemogenic susceptability in therapy-related myelodysplasia and leukemia," *Genes, Chromosomes, and Cancer* 34(2): 243-248, Kolomietz et al. (2002) "The Role of Alu Repeat Clusters as Mediators of Recurrent Chromosomal Aberrations in Tumors," *Genes, Chromosomes, and Cancer* 35(1): 97-112, and Andrew et al. (2001) "DNA Instability and Human Disease," *American Journal of Pharmacogenomics* 1(1):21-28, which are each incorporated by reference.

TABLE I

| GENE | GENBANK ACCESSION NUMBER | CODING REPEAT | EXEMPLARY DISEASE ASSOCIATIONS |
|---|---|---|---|
| ACTRII | D31770 | A8 | Colon cancer |
| AIM2 | O14862 | A10 | Colon cancer |
| APAF-1 | AJ243011 | A8 | Stomach cancer |
| APC | M74088 | A3-T-A4 | Colon cancer |
| AXIN-2 | AF205888 | A6*2, G7, C6 | Colon cancer |
| BAX | AY893312 | G8 | Hereditary Non-Polyposis Colorectal Cancer (HNPCC) |
| BCL-10 | AJ006288 | A8 | Colon cancer |
| BLM | P54132 | A9 | Stomach cancer |
| Caspase-5 | P51878 | A10 | Colon cancer |
| CDX2 | U51096 | G7 | Colon cancer |
| CHK1 | O14757 | A9 | Colon cancer |
| E2F4 | AF250378 | AG-C13 | Gastrointestinal cancer |
| FAS | X63717 | T7 | Colon cancer |
| FRAXA/FMR | BC038998 | (CGG) 50-200 | Fragile X Syndrome |
| GRB-14 | L76687 | A9 | Colon cancer |
| hG4-1 | Q81493 | A8 | Colon cancer |
| hMSH2 | L47581 | A26 (BAT-26) | Colon cancer |
| C-Kit | M60347 | T25 (BAT-25) | Colon cancer |
| IGFIIR | AF109291 | G8 | Stomach cancer |
| KIAAO977 | AL049843 | T9 | Colon cancer |
| MBD-4 | AF072250 | A10 | Colon cancer |
| MLH3 | AB039667 | A9 | HNPCC |
| MSH3 | AY275681 | A8 | HNPCC |
| MSH6 | U54777 | C8 | Stomach cancer |
| NADH-UOB | AF044416 | T9 | Colon cancer |
| OGT | AJ315767 | T10 | Colon cancer |
| PTEN | AF143315 | A6*2 | Colon cancer |
| RAD-50 | U63139 | A9 | Stomach cancer |
| RHAMM | U29343 | A9 | Colon cancer |
| RIZ | U17838 | A8, A9 | Stomach cancer |
| SEC63 | AF100141 | A10, A9 | Colon cancer |
| SLC23AI | AF092511 | C9 | Colon cancer |
| TCF-4 | AJ270770 | A9 | HNPCC |
| TGFbetaRII | AY675319 | A10 | Colon cancer |
| WISP-3 | AF100781 | A9 | Colon cancer |

Note, that the column entitled "Exemplary Disease Association" in Table I lists only one of potentially many disease states that may correlate with mutant forms of the corresponding coding repeats.

In some embodiments, for example, the repetitive nucleotide sequence or microsatellite comprises at least one mononucleotide repeat (e.g., a monomorphic or a quasi-monomorphic mononucleotide repeat locus). To further illustrate, mononucleotide repeats generally include polynucleotide sequences of $A_n$, $T_n$, $G_n$, $C_n$, $U_n$, etc., where n is an integer greater than 1. Examples of mononucleotide repeats include BAT-25 repeats and BAT-26 repeats, among many others (Hardisson et al. (2003) "Tissue microarray immunohistochemical expression analysis of mismatch repair (hMLH1 and hMSH2 genes) in endometrial carcinoma and atypical endometrial hyperplasia: relationship with microsatellite instability," *Mod Pathol.* 16(11):1148-1158, which is incorporated by reference). A subsequence of exon 5 of the human mutator hMSH2 gene is provided in FIG. 1, which is described further above. The non-mutant form of BAT-26, for example, includes a mononucleotide repeat having 26 dAs, while length polymorphisms from 10 to 22 dAs for this locus have been associated with, e.g., colon cancer (see, e.g., Pucciarelli et al. (2003) "Early-age-at-onset colorectal cancer and microsatellite instability as markers of hereditary non-polyposis colorectal cancer," *Dis Colon Rectum* 46(3):305-312, which is incorporated by reference).

Target nucleic acids including repetitive nucleotide sequences other than mononucleotide repeats are also optionally analyzed as described herein. Other exemplary repetitive nucleotide sequences of target nucleic acids include those having repeats, such as $(AT)_n$, $(GC)_n$, $(CGG)_n$, $(CGC)_n$, $(TAT)_n$, $(ATT)_n$, and/or complementary repeats thereof, where n is an integer greater than 1.

Sample preparation and target nucleic acid amplification are described further below.

IV. Probe Nucleic Acids

The probe nucleic acids of the invention bind to repetitive nucleotide sequences selected for analysis. These probe nucleic acids typically include nucleotide sequences that are at least substantially complementary to at least a portion of a non-mutant form of a repetitive nucleotide sequence, such as a non-mutant microsatellite locus. In some embodiments, these nucleotide sequences are longer than the non-mutant form of the repetitive nucleotide sequence. The probe nucleic acids of the invention generally dissociate bimodally from bound target nucleic acids that include mutant forms of repetitive nucleotide sequences under varied conditions, such as ranges of temperature used as part of melting point analyses. In contrast, these probes typically dissociate with a single mode from target nucleic acids that include non-mutant forms of the repetitive nucleotide sequences under the same conditions. These differential modes of dissociation are used to detect MSI in certain embodiments of the invention.

The probes of the invention include various embodiments, which are each optionally utilized to detect target nucleic acids. In some embodiments, for example, probes include fluorescent labels that fluoresce with increasing intensity as the probes dissociate from target nucleic acids to which they are hybridized. Examples of these types of probes nucleic acids include those with a sequence selected from SEQ ID NOS: 1-4, a substantially identical variant thereof (e.g., a sequence that includes one or more insertions, deletions, and/or substitutions relative to the sequences selected from SEQ ID NOS: 1-4) in which the variant has at least 80% sequence identity to one of SEQ ID NOS: 1-4, and complements of SEQ ID NOS: 1-4 and the variant. SEQ ID NOS: 1-4 are shown in Table II and FIG. 6.

TABLE II

| SEQ ID NO | SEQUENCE All sequences written 5' to 3' |
|---|---|
| 1 | CCUUUUUUUUUUUUUUUUUUUUUUUUUACCTG |
| 2 | TTTTTTTTTTTTTTTTTTTTTTTTT |

TABLE II-continued

| SEQ ID NO | SEQUENCE All sequences written 5' to 3' |
|---|---|
| 3 | CCUUUUUUUUUUUUUUUUUUUUUUUUUUUUUACCTG |
| 4 | CCUUUUUUUUUUUUUUUUUUUACCTG |

U = 5-propynyl-dU

These exemplary probes are optionally utilized in assays that detect the microsatellite marker, BAT-26, which is found within exon 5 of the human mutator hMSH2 gene. Examples that illustrate the use of certain of these probes are provided below. Other exemplary probe formats that are optionally adapted for use in performing the methods described herein include molecular beacons and FRET probe pairs. Molecular beacons include fluorophore-quencher pairs in which emitted fluorescence becomes quenched as the probes dissociate from targeted repetitive nucleotide sequence loci. Molecular beacons are also described in, e.g., Tsourkas et al. (2003) "Shedding light on health and disease using molecular beacons," *Brief Funct Genomic Proteomic.* 1(4):372-384, Fang et al. (2002) "Molecular beacons: fluorogenic probes for living cell study," *Cell Biochem Biophys.* 37(2):71-81, and Broude (2002) "Stem-loop oligonucleotides: a robust tool for molecular biology and biotechnology," *Trends Biotechnol.* 20(6):249-256, which are each incorporated by reference. To further illustrate, fluorescence resonance energy transfer (FRET) hybridization probes are also optionally adapted for use in detecting target nucleic acids as described herein. FRET hybridization probe formats typically utilize pairs of hybridization probes, each probe including a fluorescent label, which together act as a FRET pair when both probes are hybridized adjacent to one another on a target nucleic acid. Upon dissociation from target nucleic acids, detectable fluorescence emitted from the probes increases. FRET hybridization probes are also described in, e.g., International Patent Publication No. WO 97/46714, entitled "MONITORING HYBRIDIZATION DURING PCR," published Dec. 11, 1997 by Rasmussen et al., which is incorporated by reference. Probe design and labeling is described further below.

In some embodiments, the probe nucleic acids of the invention include modified nucleotide substitutions. The introduction of modified nucleotide substitutions into probe sequences can, e.g., stabilize helices (e.g., triplexes and duplexes), improve mismatch discrimination in high G-C content oligonucleotides, and/or the like. In certain embodiments, this can yield greater sensitivity relative to corresponding unmodified oligonucleotides even in the presence of one or more mismatches in sequence between the target nucleic acid and the probe. Examples of probes having modified nucleotide substitutions are provided in Table II. Exemplary modified nucleotides that can be substituted in the probe nucleic acids of the invention include, e.g., C5-ethyl-dC, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-0-methyl Ribo-U, 2'-0-methyl Ribo-C, an 8-aza-dA, an 8-aza-dG, a 7-deaza-dA, a 7-deaza-dG, N4-ethyl-dC, N6-methyl-dA, etc.

To further illustrate, other examples of modified nucleotide substitutions include oligonucleotides having one or more LNA™ monomers. Nucleotide analogs such as these are described further in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbæk, DK). Additional nucleotide modifications are referred to herein, including in the definitions provided above. It will be appreciated that many of these modifications are also optionally incorporated into primer nucleic acids used in performing the methods of the present invention. Other aspects of the probes and primers utilized as described herein, including synthesis and labeling, are provided below.

Although other lengths are optionally utilized, the probes of the invention generally comprise sequences that are typically between about 12 and about 100 nucleotides in length, more typically between about 15 and about 75 nucleotides in length, still more typically between about 20 and about 50 nucleotides in length, and even more typically between about 25 and about 35 nucleotides in length. Probes that have nucleotide sequences that are longer than targeted substantially complementary repetitive nucleotide sequences typically extend beyond those sequences by between about one and about 20 nucleotides, more typically by between about two and about 15 nucleotides, and still more typically by between about three and about 10 nucleotides. Methods of preparing probes, such as nucleic acid synthesis, are described further below.

Various approaches can be utilized by one of skill in the art to design probes that hybridize to a particular target repetitive nucleotide sequence. To illustrate, the DNAstar software package available from DNASTAR, Inc. (Madison, Wisc.) can be used for sequence alignments. For example, nucleic acid sequences that include target repetitive nucleotide sequences and non-target sequences can be uploaded into DNAstar EditSeq program as individual files. To further illustrate, pairs of sequence files can be opened in the DNAstar MegAlign sequence alignment program and the Clustal W method of alignment can be applied. The parameters used for Clustal W alignments are optionally the default settings in the software. MegAlign typically does not provide a summary of the percent identity between two sequences. This is generally calculated manually. From the alignments, regions having, e.g., less than 85% identity with one another are typically identified and oligonucleotide sequences in these regions can be selected. Many other sequence alignment algorithms and software packages are also optionally utilized. Sequence alignment algorithms are also described in, e.g., Mount, *Bioinformatics: Sequence and Genome Analysis*, Cold Spring Harbor Laboratory Press (2001), and Durbin et al., *Biological Sequence Analysis: Probabilistic Models of Proteins and Nucleic Acids*, Cambridge University Press (1998), which are both incorporated by reference.

To further illustrate, optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, which are each incorporated by reference, and by computerized implementations of these algorithms (GAP, BESTFIT, FASTA, and TFASTA in the Wisconsin Genetics Software Package, Genetics Computer Group (Madison, Wisc.), or by even by visual inspection.

Another example algorithm that is suitable for determining percent sequence identity is the BLAST algorithm, which is described in, e.g., Altschul et al. (1990) *J. Mol. Biol.* 215:403-410, which is incorporated by reference. Software for performing versions of BLAST analyses is publicly available through the National Center for Biotechnology Information on the world wide web at ncbi.nlm.nih.gov/ as of Jul. 25, 2005. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc. Natl. Acad. Sci. USA* 89:10915, which is incorporated by reference).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5787, which is incorporated by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, homologous) if the smallest sum probability in a comparison of the test nucleic acid to the reference nucleic acid is less than about 0.1, or less than about 0.01, and or even less than about 0.001.

Probes and other nucleic acids, such as primers, used as described herein are optionally prepared using essentially any technique known in the art. In some embodiments, for example, cloning and restriction digestion processes are utilized to prepare desired oligonucleotides. To further illustrate, probes and primers are optionally synthesized chemically using various nucleic acid synthesis methods including, e.g., according to the solid phase phosphoramidite method described by, e.g., Letsinger et al. (1976) "Synthesis of thymidine oligonucleotides by phosphite triester intermediates," *J Am Chem Soc.* 98(12):3655-3661 and Beaucage et al. (1981) "Deoxynucleoside phosphoramidites: A new class of key intermediates for deoxypolynucleotide synthesis," *Tetrahedron Lett.* 22:1859-1862, which are both incorporated by reference. In addition, oligonucleotides can also be synthesized using a diester method (see, e.g., Brown et al. (1979) "Chemical synthesis and cloning of a tyrosine tRNA gene," *Methods Enzymol.* 68:109-151, which is incorporated by reference), or a triester method (see, e.g., Capaldi et al. (2000) "Highly efficient solid phase synthesis of oligonucleotide analogs containing phosphorodithioate linkages" *Nucleic Acids Res.* 28(9):e40, Eldrup et al. (1994) "Preparation of oligodeoxyribonucleoside phosphorodithioates by a triester method" *Nucleic Acids Res.* 22(10):1797-1804, and Narang et al. (1979) "Improved phosphotriester method for the synthesis of gene fragments," *Methods Enzymol.* 68:90-98, which are each incorporated by reference). Other synthesis techniques known in the art can also be utilized including, e.g., using an automated synthesizer as described in Needham-VanDevanter et al. (1984) "Characterization of an adduct between CC-1065 and a defined oligodeoxynucleotide duplex," *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized.

The probes described herein are optionally labeled to permit detection of, e.g., amplicons, target nucleic acids, and the like. In general, a label can be any moiety that can be attached to a nucleic acid and provide a detectable signal (e.g., a quantifiable signal). Labels may be attached to probes directly or indirectly by a variety of techniques known in the art. To illustrate, depending on the type of label used, the label can be attached to a terminal (5' or 3' end of a probe) or a non-terminal nucleotide, and can be attached indirectly through linkers or spacer arms of various sizes and compositions. Using commercially available phosphoramidite reagents, one can produce probes containing functional groups (e.g., thiols or primary amines) at either the 5' or 3' terminus via an appropriately protected phosphoramidite, and can label such oligonucleotides using protocols described in, e.g., Innis et al. (Eds.) *PCR Protocols: A Guide to Methods and Applications*, Elsevier Science & Technology Books (1990), which is incorporated by reference.

Essentially any labeling moiety is optionally utilized to label nucleic acids by techniques well known in the art. In some embodiments, for example, labels comprise a fluorescent dye (e.g., a rhodamine dye (e.g., R6G, R110, TAMRA, ROX, JA270, LC610, LC640, etc.), a fluorescein dye (e.g., JOE, VIC, TET, HEX, FAM, etc.), a halofluorescein dye, a cyanine dye (e.g., CY3, CY3.5, CY5, CY5.5, LC670, LC705, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg., USA), Amersham Biosciences Corp. (Piscataway, N.J., USA), Applied Biosystems (Foster City, Calif., USA), Roche Applied Sciences, Indianapolis, Ind., USA), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference.

To further illustrate, essentially any nucleic acid (and virtually any labeled nucleic acid, whether standard or non-standard) can be custom or standard ordered from any of a variety of commercial sources, such as The Midland Certified Reagent Company (Midland, Tex., USA), Operon Technologies Inc. (Alameda, Calif., USA), Proligo LLC (Boulder, Calif., USA), Sigma-Genosys (The Woodlands, Tex., USA), and many others.

In certain embodiments, probes designed to hybridize with target nucleic acids are covalently or noncovalently attached to solid supports. In these embodiments, labeled amplicons derived from target nucleic acids are typically contacted with these solid support-bound probes to effect hybridization and detection. In other embodiments, amplicons are attached to solid supports and contacted with labeled probes. In still other embodiments, nucleic acids are detected free in solution.

Essentially any substrate material is optionally adapted for use as a solid support. In certain embodiments, for example, substrates are fabricated from silicon, glass, or polymeric materials (e.g., glass or polymeric microscope slides, silicon wafers, wells of microwell plates, etc.). Suitable glass or polymeric substrates, including microscope slides, are available from various commercial suppliers, such as Fisher Scientific (Pittsburgh, Pa., USA) or the like. In some embodiments, solid supports utilized in the invention are membranes. Suitable membrane materials are optionally selected from, e.g. polyaramide membranes, polycarbonate membranes, porous plastic matrix membranes (e.g., POREX® Porous Plastic, etc.), nylon membranes, ceramic membranes, polyester membranes, polytetrafluoroethylene (TEFLON®) membranes, polypropylene membranes, nitrocellulose membranes, or the like. Many of these membranous materials are widely available from various commercial suppliers, such as, P. J. Cobert Associates, Inc. (St. Louis, Mo., USA), Millipore Corporation (Bedford, Mass., USA), or the like. Other exemplary solid supports that are optionally utilized include, e.g., ceramics, metals, resins, gels, plates, beads (e.g., magnetic microbeads, etc.), whiskers, fibers, combs, single crystals, self-assembling monolayers, and the like.

Nucleic acids are directly or indirectly (e.g., via linkers, such as bovine serum albumin (BSA) or the like) attached to the supports, e.g., by any available chemical or physical method. A wide variety of linking chemistries are available for linking molecules to a wide variety of solid supports. More specifically, nucleic acids may be attached to the solid support by covalent binding, such as by conjugation with a coupling agent or by non-covalent binding, such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (Sano et al. (1991) *Bio/Technology* 9:1378, which is incorporated by reference), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative.

Cleavable attachments can be created by attaching cleavable chemical moieties between the probes and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds, which can be cleaved by proteases, and phosphodiester bonds, which can be cleaved by nucleases.

Chemical agents such as β-mercaptoethanol, dithiothreitol (DTT) and other reducing agents cleave disulfide bonds. Other agents that may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

A number of array systems have been described and can be adapted for use in the detection of target nucleic acids. Aspects of array construction and use are also described in, e.g., Sapolsky et al. (1999) "High-throughput polymorphism screening and genotyping with high-density oligonucleotide arrays" *Genetic Analysis: Biomolecular Engineering* 14:187-192, Lockhart (1998) "Mutant yeast on drugs" *Nature Medicine* 4:1235-1236, Fodor (1997) "Genes, Chips and the Human Genome" *FASEB Journal* 11:A879, Fodor (1997) "Massively Parallel Genomics" *Science* 277: 393-395, and Chee et al. (1996) "Accessing Genetic Information with High-Density DNA Arrays" *Science* 274:610-614, all of which are incorporated by reference.

V. Reaction Mixtures

The reaction mixtures of the invention are typically used to perform hybridization probe melting point analyses to identify mutant or non-mutant forms of one or more target nucleic acids. Thus, in addition to the probes described herein, reaction mixtures also typically include target nucleic acids and/or amplicons of the target nucleic acids. In embodiments where a single target repetitive nucleotide sequence locus is to be assayed, only a single probe type is typically included in the mixture. In multiplexing formats where multiple target loci are to be concurrently evaluated, probes corresponding to each of the target loci are generally included in the reaction mixtures. In these embodiments, the various probe types typically include different labeling moieties to facilitate the separate detection of the dissociation of each probe from its corresponding target nucleic acid in the reaction mixture. Nucleic acid labeling is described further above. Although other concentrations are optionally utilized, probes and target nucleic acids and/or amplicons of those targets are each generally present in the reaction mixtures at concentrations between about 100 nM and about 1.5 μM (i.e., between about 10 pmol and about 150 pmol in 100 μL of the reaction mixtures).

In some embodiments, reaction mixtures also include various additional components that act to facilitate melting point analyses. For example, reaction mixtures optionally include salts (e.g., NaCl, KCl, and/or the like). In these embodiments, a concentration of the salt in the reaction mixture is typically between about 10 mM and about 100 mM. In certain embodiments, reaction mixtures also include buffers. Buffers are typically used to maintain a pH of the reaction mixtures between about 5.5 and about 10.0. Exemplary buffers that are optionally utilized include one or more of, e.g., tris-(hydroxymethyl)aminoethane, tris-(hydroxymethyl)aminomethane sodium phosphate, bis(2-hydroxyethyl)-iminotris(hydroxymethyl)methane, sodium acetate, sodium citrate, sodium tetraborate, glycine-sodium hydroxide, N-2-hydroxyethylpiperazine-N'-2-ethanesulfonic acid, 3-[(1,1-dimethyl-hydroxyethyl)amino]-2-hydroxypropanesulfonic acid, 3-(cyclohexylamino)-2-hydroxy-1-propanesulfonic acid, 3-[N,N-bis(hydroxyethyl)amino]-2-hydroxypropanesulfonic acid, N-(2-hydroxyethyl)piperazine-N'-2-hydroxy propanesulfonic acid, 3-(N-morpholino)-2-hydroxypropanesulfonicsulfonic acid, piperazine-N,N'-bis(2-hydroxypropanesulfonic acid), 3-[N-tris-(hydroxymethyl)methyl amino]-2-hydroxypropanesulfonic acid, 2-(N-morpholino)-ethanesulfonic acid, 3-(N-morpholino)propanesulfonic acid, piperazine-N,N'-bis(ethanesulfonic acid), or the like. In these embodiments, a concentration of the buffer in a given reaction mixture is generally between about 5 mM and about 100 mM. Reaction mixtures also optionally include cofactors, such as $Mg^{2+}$ (e.g., $MgSO_4$, $MgCl_2$, etc.), $Mn^{2+}$ (e.g., $MnSO_4$, $MnCl_2$, etc.), and/or the like. In these embodiments, a concentration of the cofactor in a reaction mixture is typically between about 0.1 mM and about 25 mM.

To further illustrate, an exemplary reaction mixture includes as follows:

50 mM KCl;
10 mM Tris-HCl (pH 8.3-9.0);
1.5 mM $MgCl_2$;
40 pmol probe nucleic acid (400 nM in 100 μL of the reaction mixture); and
40 pmol target nucleic acid (400 nM in 100 μL of the reaction mixture).

The selected target nucleic acids are generally amplified prior to performing hybridization probe melting point analyses. In embodiments where targets are amplified before being subjected to further analysis, the amplicons are optionally separated from other amplification reagents or otherwise purified by methods well-known to those of skill in the art (e.g., electrophoretically, chromatographically, etc.) prior to being added to the reaction mixtures that include the probes.

Essentially any nucleic acid amplification technique can be used to amplify or co-amplify selected target nucleic acids. In certain embodiments, reaction mixtures used to amplify nucleic acids include nucleotide incorporating biocatalysts (e.g., DNA polymerases, RNA polymerases, DNA ligases, etc.), primer nucleic acids, and probe nucleic acids (e.g., 5'-nuclease probes, molecular beacons, or the like for "real-time" monitoring) in addition to various other reagents that may be useful in performing a particular amplification process (e.g., extendible nucleotides, pyrophosphatases, uracil N-glycosylase (UNG), buffers, salts, glycerol, metal ions, dimethyl sulfoxide (DMSO), poly rA, and the like.

Persons of skill in the art can readily select primers that are suitable for the amplification of individual microsatellite loci. Moreover, exemplary guidance regarding oligonucleotide design and synthesis is described above. To illustrate, however, exemplary primers that may be useful in amplifying selected loci are provided in Table III and FIG. 6.

TABLE III

| LOCUS | GENBANK ACCESSION NO. | PRIMER SEQ ID NO. |
|---|---|---|
| BAT-25 | U63834 | 17, 18, 19 |
| BAT-26 | U41210 | 20, 21, 22, 23 |
| BAT-40 | M38180 | 24, 25 |
| D7S1808 | G08643 | 26, 27, 28, 29 |
| D10S1426 | G08812 | 30, 31, 32, 33 |
| D3S2432 | G08240 | 34, 35, 36 |
| D7S3046 | G10353 | 37, 38, 39, 40 |
| D7S3070 | G27340 | 41, 42, 43, 44 |
| MONO-15 | AC007684 | 45, 46, 47, 48 |
| D1S518 | G07854 | 49, 50, 51, 52 |

Nucleic acid amplification reaction mixtures are generally produced by combining selected nucleotide incorporating biocatalysts and primer nucleic acids with quantities of selected nucleic acid amplification reagents that are sufficient for performing the particular nucleic acid extension or amplification method to be undertaken. Methods of preparing target nucleic acids and the quantities of nucleic acid amplification reagents to be included in a given reaction mixture are well known to persons of skill in the art in view of the selected nucleic acid extension or amplification method. To illustrate, however, primer nucleic acids and extendible nucleotides (e.g., four dNTPs (dGTP, dCTP, dATP, dTTP)) are each typically present in a large molar excess in the reaction mixtures of the invention.

The nucleotide incorporating biocatalysts utilized in the nucleic acid amplification reaction mixtures and other aspects of the invention typically comprise enzymes, such as polymerases (e.g., DNA polymerases, RNA polymerases, etc.), terminal transferases, reverse transcriptases, telomerases, polynucleotide phosphorylases, ligases, and the like. Suitable nucleotide incorporating biocatalysts are enzymes known to catalyze primer and template-dependent DNA synthesis and typically possess a 5' to 3' nuclease activity, e.g., for performing 5'-nuclease reactions to effect "real-time" monitoring. Exemplary DNA polymerases of this type include *E. coli* DNA polymerase I, Tth DNA polymerase, *Bacillus stearothermophilus* DNA polymerase, Taq DNA polymerase, *Thermus* sp. ZO5 DNA polymerase, *Thermatoga maritima* DNA polymerase, *Thermatoga neopolitana* DNA polymerase, and *Thermosipho africanus* DNA polymerase. Derivatives of these enzymes that possess other properties (e.g., fluorescent dye-labeled nucleotide incorporation, ribonucleotide incorporation, etc.) may also be utilized as desired. The reaction conditions for catalyzing DNA synthesis with these DNA polymerases are well known to persons of skill in the art.

Thermostable polymerases are typically used in automated processes that effect the denaturation of double stranded extension products by exposing them to a elevated temperatures (e.g., about 95° C.) during the PCR cycle. For example, U.S. Pat. No. 4,889,818, entitled "PURIFIED THERMOSTABLE ENZYME," issued to Dec. 26, 1989 to Gelfand et al., which is incorporated by reference, discloses a representative thermostable enzyme isolated from *Thermus aquaticus*. Additional representative thermostable polymerases include, e.g., polymerases extracted from the thermostable bacteria *Thermus flavus*, *Thermus ruber*, *Thermus thermophilus*, *Bacillus stearothermophilus* (which has a somewhat lower temperature optimum than the others listed), *Thermus lacteus*, *Thermus rubens*, *Thermotoga maritima*, *Thermatoga neopolitana*, *Thermosipho africanus*, *Thermococcus littoralis*, and *Methanothermus fervidus*.

In certain embodiments, additional reagents are also added to nucleic acid amplification reaction mixtures. To illustrate, these reaction mixtures also optionally include pyrophosphatases (e.g., a thermostable pyrophosphatase), e.g., for use in minimizing pyrophosphorolysis, dUTP and uracil N-glycosylase (UNG) (e.g., AMPERASE®, which is commercially available from Roche Diagnostics Corporation (Indianapolis, Ind., USA), etc.), e.g., to protect against carry-over contamination, and the like.

VI. Methods of Detecting Mutant Forms of Target Nucleic Acids

The methods of the invention provide for the detection of mutant forms of target nucleic acids having repetitive nucleotide sequences. For example, these methods can be used to assess microsatellite instability at one or more loci in a given genome. This can provide information to a subject from which target nucleic acids are obtained, such as a predisposition to a particular disease state, a diagnosis of a given genetic disorder, or the like. The methods generally include binding (e.g., hybridizing, etc.) probe nucleic acids to target nucleic acids and detecting a bimodal dissociation of the probe nucleic acids from the target nucleic acids under at least one varied condition, such as a varied temperature utilized as part of a melting point analysis. Detected bimodal dissociations, e.g., in the form of bimodal distributions of melting peaks for particular probes generally correlates with mutant forms of the target nucleic acids under analysis. In certain embodiments, the detection of non-bimodal dissociations is indicative of the presence of non-mutant genotypes. To increase the quantity of a given target nucleic acid to be assayed, that target is typically amplified prior to detecting probe:target dissociation.

Genomic DNA amplified or co-amplified according to the methods described herein generally originates from biological material from an individual subject, typically a mammal, such as a human, a dog, a cat, a horse, a sheep, a mouse, a rat, a rabbit, a monkey, or the like. The biological material can be any tissue, cells, or biological fluid from the subject, which contains genomic DNA. The biological material is typically selected from, e.g., tumor tissue, disseminated cells, feces, blood cells, blood plasma, serum, lymph nodes, urine, and other bodily fluids.

Samples of biological material are obtained using essentially any collection technique. In some embodiments, for example, stool or urine samples are collected from patients, whereas in others, swabs, brushes, or loops are utilized to take samples from, e.g., the endocervix, the urethra, the rectum, the vagina, the oropharynx, an eye, etc. of the particular patient. A number of swab types are suitable for collecting these samples, including rayon fibre-tipped swabs, cotton swabs, DACRON® swabs, or the like. Optionally, swabs are coated (e.g., serum or bovine albumin-coated swabs, calcium-alginate swabs, etc.). Urine or swabbed specimens are typically placed into sample containers, such as polypropylene tubes, screw-cap plastic tubes, and the like. The biological material is optionally in the form of tissue samples fixed in formalin and embedded in paraffin (PET). Tissue samples from biopsies are commonly stored in PET for long term preservation. In addition, blood samples are typically obtained via venipuncture. Methods of storing specimens, culturing cells, isolating and preparing target nucleic acids from these sources are generally known to persons of skill in the art.

Amplification methods that are optionally utilized to amplify target nucleic acids in or from the samples of biological material include, e.g., various polymerase, ligase, or reverse-transcriptase mediated amplification methods, such as the polymerase chain reaction (PCR), the ligase chain reaction (LCR), reverse-transcription PCR (RT-PCR), and/or the like. Details regarding the use of these and other amplification methods can be found in any of a variety of standard texts, including, e.g., Berger, Sambrook, Ausubel 1 and 2, and Innis, which are referred to above. Many available biology texts also have extended discussions regarding PCR and related amplification methods. Nucleic acid amplification is also described in, e.g., Mullis et al., (1987) U.S. Pat. No. 4,683,202 and Sooknanan and Malek (1995) *Biotechnology* 13:563, which are both incorporated by reference. Improved methods of amplifying large nucleic acids by PCR are summarized in Cheng et al. (1994) *Nature* 369:684, which is incorporated by reference. In certain embodiments, duplex PCR is utilized to amplify target nucleic acids. Duplex PCR amplification is described further in, e.g., Gabriel et al. (2003) "Identification of human remains by immobilized sequence-specific oligonucleotide probe analysis of mtDNA hypervariable regions I and II," *Croat. Med. J.* 44(3)293 and La et al. (2003) "Development of a duplex PCR assay for detection of Brachyspira hyodysenteriae and Brachyspira pilosicoli in pig feces," *J. Clin. Microbiol.* 41(7):3372, which are both incorporated by reference.

Any available method for detecting target nucleic acids and/or amplicons thereof can be used, e.g., to monitor amplification reactions. Common approaches include real-time amplification detection with 5'-nuclease probes or molecular beacons, detection of intercalating dyes, detection of labels incorporated into the amplification probes or the amplified nucleic acids themselves, e.g., following electrophoretic separation of the amplification products from unincorporated label, hybridization based assays (e.g., array based assays), and/or detection of secondary reagents that bind to the nucleic acids. For example, a 5'-nuclease probe or a molecular beacon is optionally designed to include a oligonucleotide sequence that binds a particular target nucleic acid. Molecular beacons or 5'-nuclease probes are described further below. These general approaches are also described in, e.g., Sambrook, and Ausubel 1 and 2.

In certain embodiments, real-time PCR assay systems that include one or more 5'-nuclease probes are used for detecting amplified target nucleic acids. These systems operate by using the endogenous endonuclease activity of certain polymerases to cleave a quencher or label free from an oligonucleotide that comprises the quencher and label, resulting in unquenching of the label. The polymerase only cleaves the quencher or label upon initiation of replication, i.e., when the oligonucleotide is bound to the template and the polymerase extends the primer. Thus, an appropriately labeled probe nucleic acid and a polymerase comprising the appropriate nuclease activity can be used to monitor a given amplification process. Real time PCR product analysis by, e.g., FRET or the like (and related real time reverse-transcription PCR) provides a well known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12):2759-65; and Kreuzer et al. (1999) "LightCycler technology for the quantitation of bcr/abl fusion transcripts" *Cancer Research* 59(13):3171-4, all of which are incorporated by reference).

Molecular beacons are oligonucleotides designed for real time detection and quantification of target nucleic acids. The 5' and 3' termini of molecular beacons collectively comprise a pair of moieties, which confers the detectable properties of the molecular beacon. One of the termini is attached to a fluorophore and the other is attached to a quencher molecule capable of quenching a fluorescent emission of the fluorophore. To illustrate, one example fluorophore-quencher pair can use a fluorophore, such as EDANS or fluorescein, e.g., on the 5'-end and a quencher, such as Dabcyl, e.g., on the 3'-end. When the molecular beacon is present free in solution, i.e., not hybridized to a second nucleic acid, the stem of the molecular beacon is stabilized by complementary base pairing. This self-complementary pairing results in a "hairpin loop" structure for the molecular beacon in which the fluorophore and the quenching moieties are proximal to one another. In this confirmation, the fluorescent moiety is quenched by the quenching moiety. The loop of the molecular beacon typically comprises the oligonucleotide probe and is accordingly complementary to a sequence to be detected in the target nucleic acid, such that hybridization of the loop to its complementary sequence in the target forces disassociation of the stem, thereby distancing the fluorophore and quencher from each other. This results in unquenching of the fluorophore, causing an increase in fluorescence of the molecular beacon.

Details regarding standard methods of making and using molecular beacons are well established in the literature and molecular beacons are available from a number of commercial reagent sources. Further details regarding methods of molecular beacon manufacture and use are found, e.g., in Leone et al. (1995) "Molecular beacon probes combined with amplification by NASBA enable homogenous real-time detection of RNA," *Nucleic Acids Res.* 26:2150-2155; Kostrikis et al. (1998) "Molecular beacons: spectral genotyping of human alleles" *Science* 279:1228-1229; Fang et al. (1999) "Designing a novel molecular beacon for surface-immobilized DNA hybridization studies" *J. Am. Chem. Soc.* 121: 2921-2922; and Marras et al. (1999) "Multiplex detection of single-nucleotide variation using molecular beacons" *Genet. Anal. Biomol. Eng.* 14:151-156, all of which are incorporated by reference. A variety of commercial suppliers produce standard and custom molecular beacons, including Oswel Research Products Ltd. (UK), Research Genetics (a division of Invitrogen, Huntsville, Ala., USA), the Midland Certified Reagent Company (Midland, Tex., USA), and Gorilla Genomics, LLC (Alameda, Calif., USA). A variety of kits that utilize molecular beacons are also commercially available, such as the Sentinel™ Molecular Beacon Allelic Discrimination Kits from Stratagene (La Jolla, Calif., USA) and various kits from Eurogentec SA (Belgium) and Isogen Bioscience BV (Netherlands).

Amplicons are optionally recovered and purified from other reaction components by any of a number of methods well known to persons of skill in the art, including electrophoresis, chromatography, precipitation, dialysis, filtration, and/or centrifugation. Aspects of nucleic acid purification are described in, e.g., Douglas et al., *DNA Chromatography*, Wiley, John & Sons, Inc. (2002), and Schott, *Affinity Chromatography: Template Chromatography of Nucleic Acids and Proteins*, Chromatographic Science Series, #27, Marcel Dekker (1984), both of which are incorporated by reference. In certain embodiments, amplicons are not purified prior to detection, such as when probe melting point analyses are performed using nucleic acid reaction mixtures directly following amplification.

Hybridization of probes to target nucleic acids can be accomplished by choosing appropriate hybridization conditions. The stability of the probe:target nucleic acid hybrid is typically selected to be compatible with the assay and washing conditions so that stable hybrids form only between the probes and target nucleic acids. Manipulation of one or more of the different assay parameters determines the exact sensitivity and specificity of a particular hybridization assay.

More specifically, hybridization between complementary bases of nucleic acids occurs under a wide variety of conditions that vary in temperature, salt concentration, electrostatic strength, buffer composition, and the like. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about two hours, depending on the nature of the sequence to be hybridized and its length. However, it is recognized that hybridizations can occur in seconds or many hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin.

Essentially any approach to performing melting curve analyses is optionally utilized to detect the dissociation of probes from target nucleic acids to effect the detection of mutant forms of the targets as described herein. To illustrate, a melting profile can be established following target amplification by incubating the amplicons and probes together starting at a temperature of about 35° C. and increasing that temperature to about 95° C. with continuous detection at a rate of between about 0.1° C./second to about 1.0° C./second. Exemplary commercially available systems that are optionally utilized to detect target nucleic acids and/or perform nucleic acid melting curve analyses include, e.g., a LIGHT-CYCLER® system or a COBAS AMPLICOR® Analyzer, which are both available from Roche Diagnostics Corporation (Indianapolis, Ind., USA), a LUMINEX 100™ system, which is available from the Luminex Corporation (Austin, Tex., USA), and the like. Systems are also described further below.

VII. Systems

The invention also provides systems for detecting mutant forms of target nucleic acids. The systems include one or more probe nucleic acids as described herein. In certain embodiments, the probes are arrayed on a solid support, whereas in others, they are provided in one or more containers (e.g., multi-well plates, etc.), e.g., for assays performed in solution. In addition, the systems also include detectors (e.g., a spectrometer, etc.) that detect dissociation of the probe nucleic acids from selected target nucleic acids when the probe nucleic acids are bound to the target nucleic acids and subjected to one or more varied conditions, such as a range of temperatures. The systems also generally include thermal modulators (e.g., a thermal cycling device, etc.) operably connected to the containers or solid supports to modulate temperature in the containers or on the solid supports, and fluid transfer components (e.g., an automated pipettor, etc.) that transfer fluids to and/or from the containers or solid supports, e.g., for performing nucleic acid amplification processes and/or melting curve analyses in the container or on the solid support.

Detectors are typically structured to detect detectable signals produced, e.g., in or proximal to another component of the particular system (e.g., in containers, on solid supports, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond in position to "real-time" results, e.g., as part of melting curve analyses. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), which are both incorporated by reference.

The systems of the invention also typically include controllers that are operably connected to one or more components (e.g., detectors, thermal modulators, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. For example, controllers are typically configured to correlate detected bimodal dissociations of the probe nucleic acid from bound target nucleic acids with diagnoses of genetic disorders or disease states for subjects from which the target nucleic acids were obtained. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

Figure 2:
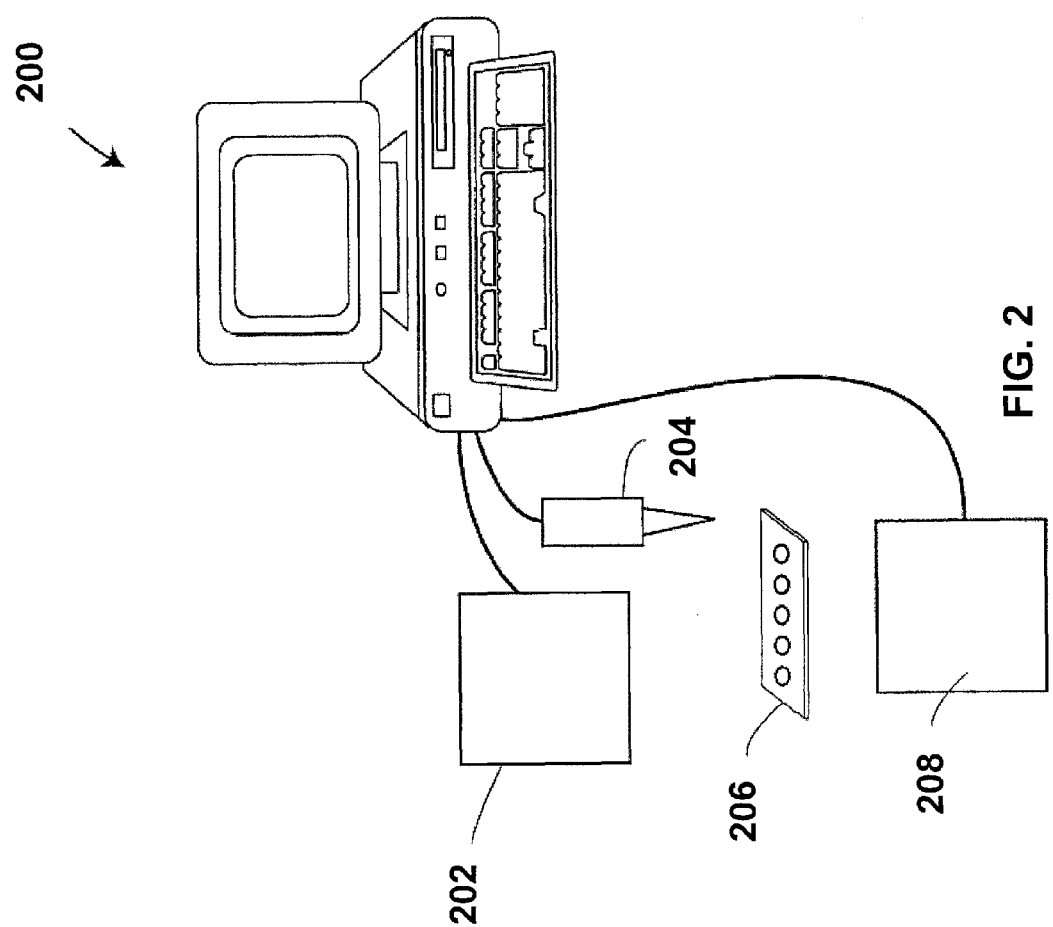
FIG. 2 is a block diagram showing a representative system according to one embodiment of the invention.

FIG. 2 is a schematic showing a representative system that includes a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

In particular, FIG. 2 schematically illustrate computer 200 to which detector 202 and fluid transfer component 204 are operably connected. Optionally, detector 202 and/or fluid transfer component 204 is operably connected to computer 200 via a server (not shown in FIG. 2). During operation, fluid transfer component 204 typically transfers fluids, such as reaction mixture components to the wells of multi-well plate 206. As additionally shown, thermal modulator 208 is also operably connected to computer 200. Thermal modulator 208 is typically used to effect thermal modulation of reaction mixtures disposed in the wells of multi-well plate 206, e.g., as part of a melting point or curve analysis. Detector 202 typically detects detectable signals (e.g., fluorescent emissions, etc.) produced by labeled probes as they dissociate from target nucleic acids in the wells of multi-well plate 206 as a given melting curve analysis is performed.

VIII. Kits

The invention also provides kits that include the probe nucleic acids described herein for performing the methods of the invention. In some embodiments, probe nucleic acids are provided in solution, whereas in others, they provided attached to a solid support. The kits also include instructions for detecting dissociation of the probe nucleic acids from bound target nucleic acids. In certain embodiments, kits also include instructions for one or more of, e.g., obtaining target nucleic acids from subjects, amplifying the target nucleic acids, binding the probe nucleic acids to the target nucleic acids, varying at least one condition (e.g., a temperature condition as part of a melting curve analysis), correlating detected bimodal dissociations with diagnoses of genetic disorders or disease states for subjects, or the like. In addition, the kits optionally also include one or more components selected from, e.g., nucleotide incorporating biocatalysts, extendible nucleotides, pyrophosphatases, uracil N-glycosylases, salts, buffers, cofactors, and the like. In some embodiments, kits also include purified nucleic acid targets that will act as positive and/or negative controls for the instrument and reagent performance. Typically, the kits also include at least one container for packaging the probe nucleic acids, the instructions, and/or one or more other components.

IX. Examples

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example 1

Nucleic Acid Melting Point Analyses

This example describes melting point analyses that were performed using various oligonucleotides. The sequences of the oligonucleotides that were used in these analyses are provided in Table IV and FIG. 6.

TABLE IV

| SEQ ID NO | OLIGONUCLEOTIDE DESIGNATION | SEQUENCE All sequences written 5' to 3' |
|---|---|---|
| 5 | CDN22 | TTAACCTTTTTCAGGTAAAAAAAAAAAAAAAAAAAAAAAAAGGGTTAAAAATGTTG |
| 6 | CDN23 | TAACCTTTTTCAGGTAAAAAAAAAAAAAAAAAAAAGGGTTAAAAATGTTG |
| 7 | CDN24 | TAACCTTTTTCAGGTAAAAAAAAAAAAAAAAAGGGTTAAAAATGTTG |
| 8 | CDN25 | TAACCTTTTTCAGGTAAAAAAAAAAAAAAGGGTTAAAAATGTTG |
| 9 | CDN26 | TAACCTTTTTCAGGTAAAAAAAAAAGGGTTAAAAATGTTG |
| 10 | CDN28 | FCCUUUUUUUUUUUUUUUUUUUUUUUUACCTGP |
| 11 | CDN29 | FTTTTTTTTTTTTTTTTTTTTTTTTTP |
| 12 | CDN30 | FCCUUUUUUUUUUUUUUUUUUUUUUUUUUUUUUACCTGP |
| 13 | CDN31 | FCCUUUUUUUUUUUUUUUUUUACCTGP |
| 14 | CDN32 | TAACCTTTTTCAGGTAAAAAAAAAAAAAAAAAAAAAAGGGTTAAAAATGTTG |
| 15 | CDN33 | TAACCTTTTTCAGGTAAAAAAAAAAAAAAAAAAAAAAAAGGGTTAAAAATGTTG |
| 16 | CDN34 | TAACCTTTTTCAGGTAAAAAAAAAAAAAAAAAAAAAAAAAAGGGTTAAAAATGTTG |

F = FAM; P = phosphate; U = 5-propynyl-dU

Each of the analyses described in this example was performed using reaction mixtures that included a PCR buffer (50 mM KCl, 1.5 mM $MgCl_2$, 10 mM TrisHCl, 0.001% gelatin, pH 8.3) in a LIGHTCYCLER® system (Roche Diagnostics Corporation, Indianapolis, Ind., USA). The particular probe and target nucleic acids that were included in the reaction mixtures used in these analyses are specified below. Melting profiles were established by incubating the reaction mixtures starting at 30° C. for 30 seconds and increasing the temperature to 95° C. at a rate of 0.1° C./second with continuous fluorescence detection at F1.

CDN29 Melting Point Analyses

The probe nucleic acid used in the melting point analyses described in this section was CDN29. The target nucleic acids included in the reaction mixtures used in these analyses were CDN22, CDN23, CDN24, CDN25, and CDN26. Each reaction mixture included 20 pmol (200 nM in 100 µL of the reaction mixture) of the CDN29 probe and 20 pmol (200 nM in 100 µL of the reaction mixture) of one of the target nucleic acids. In addition, each analysis was replicated two times.

Figure 3A:
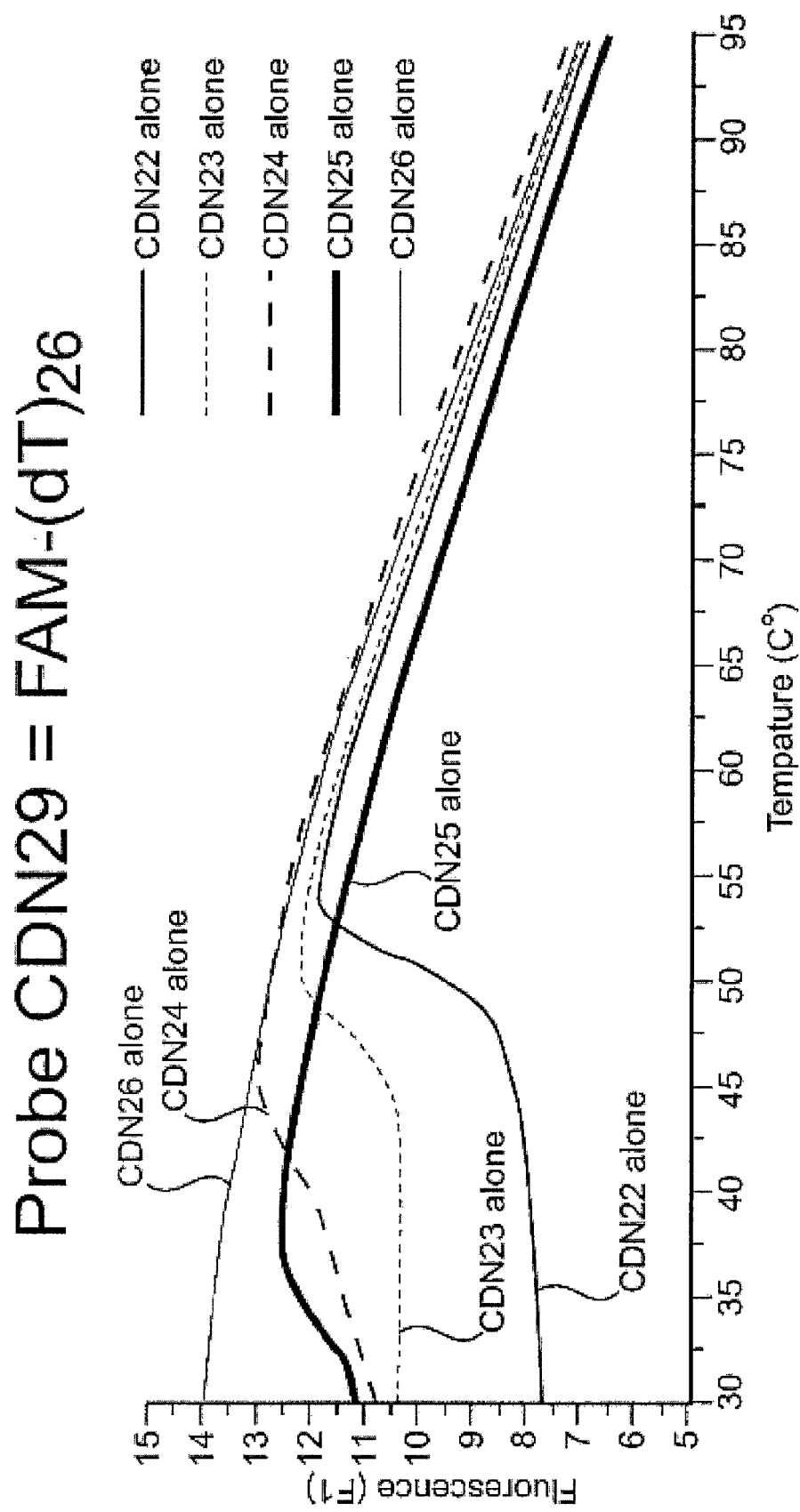
FIG. 3A provides a melting curve plot displayed as function of raw fluorescence using CDN29 as a probe nucleic acid.
Figure 3B:
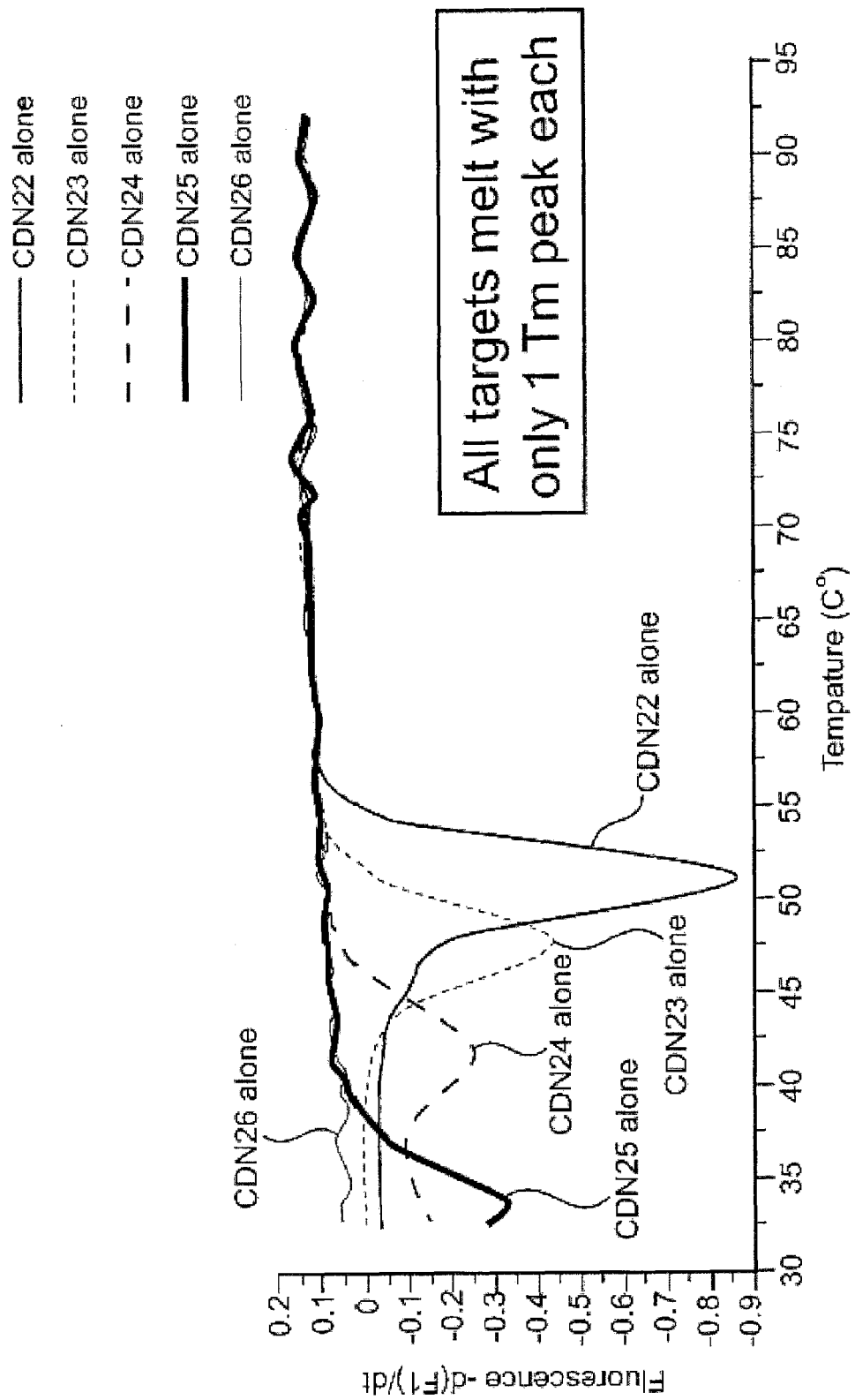
FIG. 3B provides this same data using a first derivative plot.

The results of these melting point analyses are shown in FIG. 3, panels A and B. FIG. 3, panel A is a melting curve plot of this data: in which the y-axis represents absolute fluorescence (F1) and the x-axis represents temperature (° C.). FIG. 3, panel B is a melting curve plot of this data in which the y-axis represents relative fluorescence (−d(F1)/dT) and the x-axis represents temperature (° C.). The particular target nucleic acid associated with each trace is shown in the legend that is included in FIG. 3. As shown in FIG. 3, panel B, all target nucleic acids melted with only one melting temperature ($T_m$) peak each.

CDN28 Melting Point Analyses

The probe nucleic acid used in the melting point analyses described in this section was CDN28. The target nucleic acids included in the reaction mixtures used in these analyses were CDN22, CDN23, CDN24, CDN25, CDN26, CDN32, CDN33, and CDN34. Each reaction mixture included 20 pmol (200 nM in 100 µL of the reaction mixture) of the CDN28 probe and 20 pmol (200 nM in 100 µL of the reaction mixture) of one of the target nucleic acids. In addition, each analysis was replicated two times.

Figure 4A:
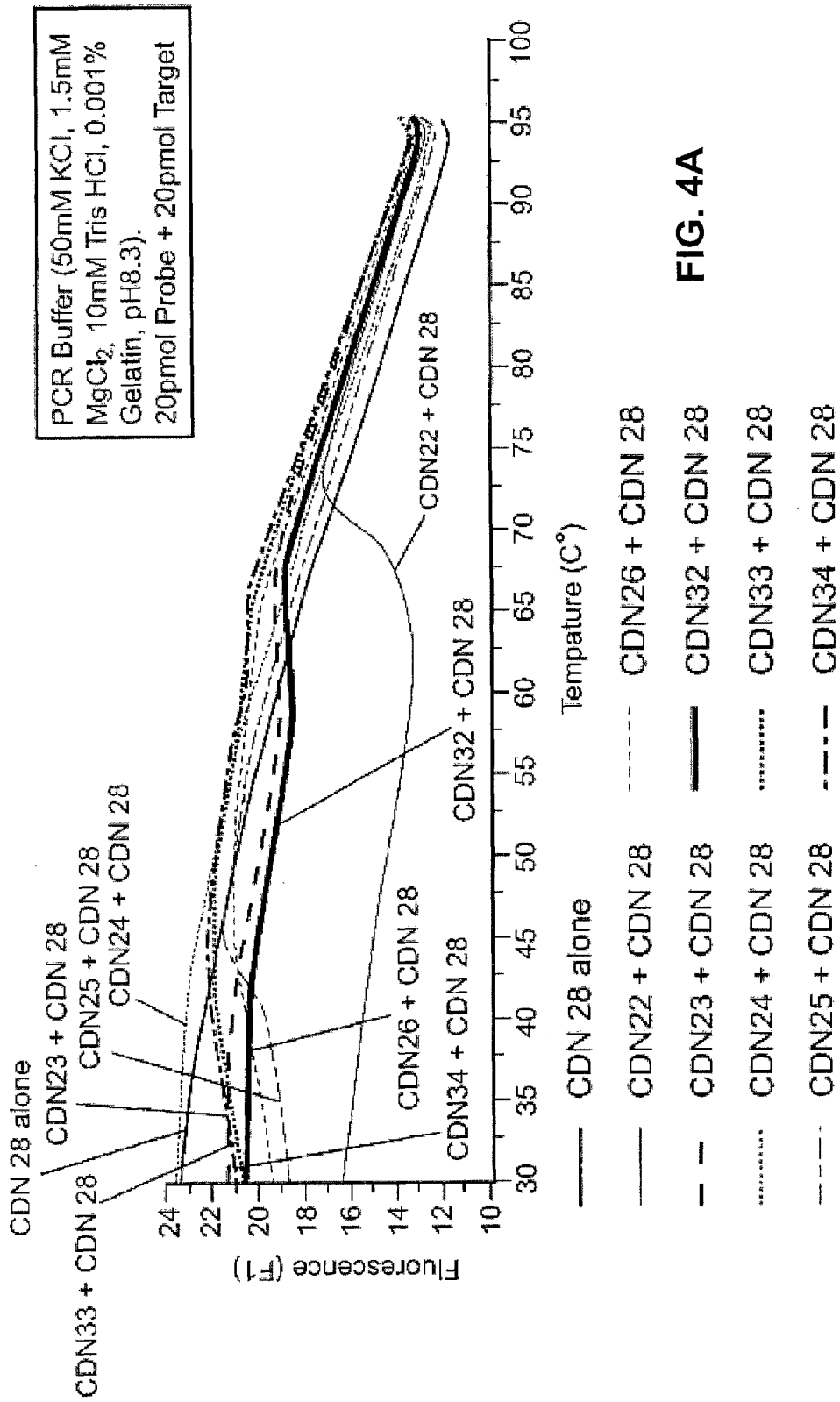
FIG. 4A provides a melting curve plot displayed as function of raw fluorescence using CDN28 as a probe nucleic acid.
Figure 4B:
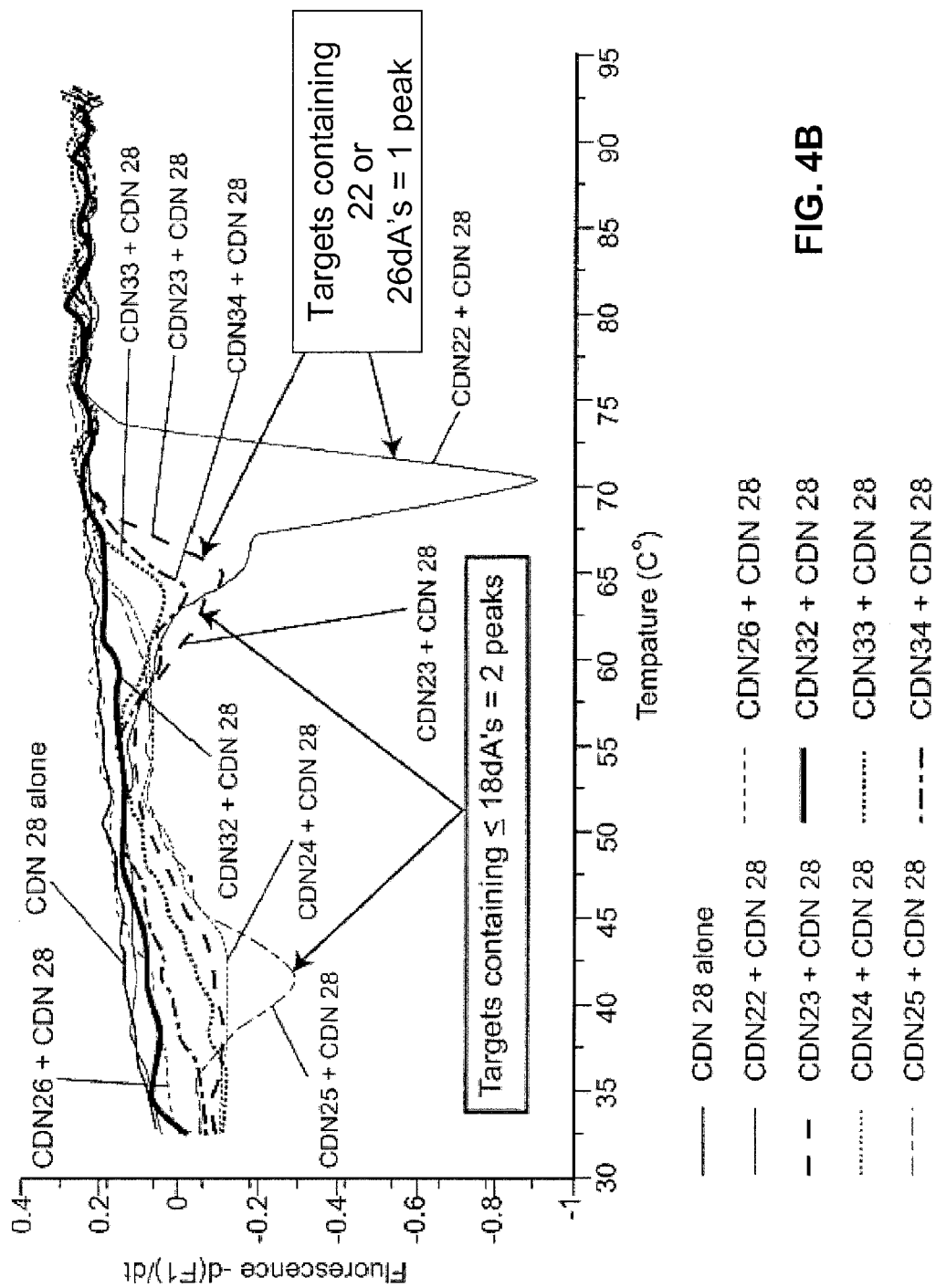
FIG. 4B provides this same data using a first derivative plot.

The results of these melting point analyses are shown in FIG. 4, panels A and B. FIG. 4, panel A is a melting curve plot of this data in which the y-axis represents absolute fluorescence (F1) and the x-axis represents temperature (° C.). FIG. 4, panel B is a melting curve plot of this data in which the y-axis represents relative fluorescence (−d(F1)/dT) and the x-axis represents temperature (° C.). The particular target nucleic acid associated with each trace is shown in the legend that is included in FIG. 4. As a negative control, the reaction mixtures of one set analyses lacked target nucleic acids. As shown in FIG. 4, panel B, target nucleic acids with repetitive nucleotide sequences having 18 dAs or fewer melted with two $T_m$ peaks each, while those with repetitive nucleotide sequences having 22 or 26 dAs melted with only one $T_m$ peak each.

CDN30 Melting Point Analyses

The probe nucleic acid used in the melting point analyses described in this section was CDN30. The target nucleic acids included in the reaction mixtures used in these analyses were CDN22, CDN23, CDN24, CDN25, CDN26, CDN32, CDN33, and CDN34. Each reaction mixture included 40 pmol (400 nM in 100 µL of the reaction mixture) of the CDN30 probe and 40 pmol (400 nM in 100 μL of the reaction mixture) of one of the target nucleic acids. In addition, each analysis was replicated two times.

Figure 5A:
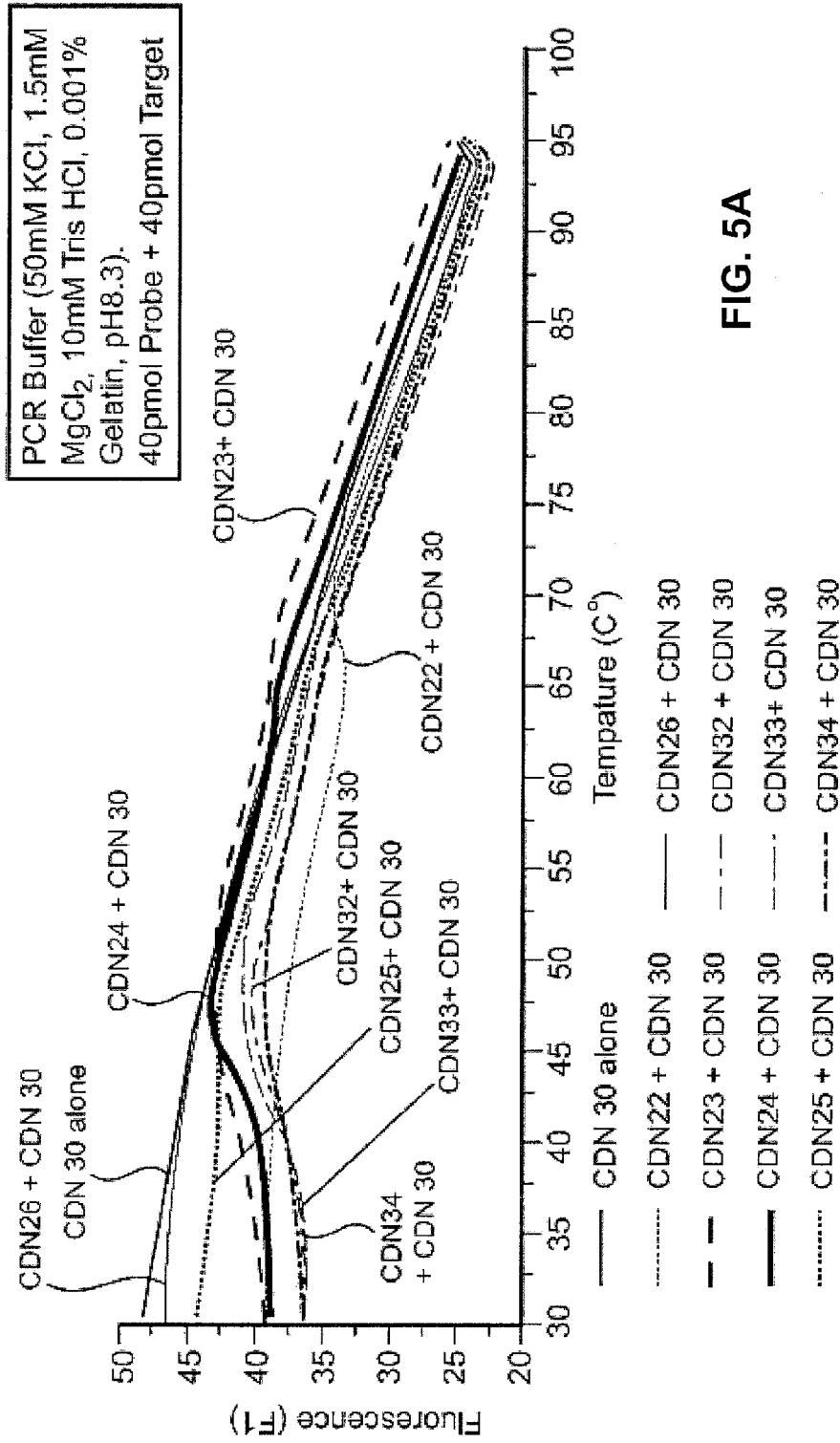
FIG. 5A provides a melting curve plot displayed as function of raw fluorescence using CDN30 as a probe nucleic acid.
Figure 5B:
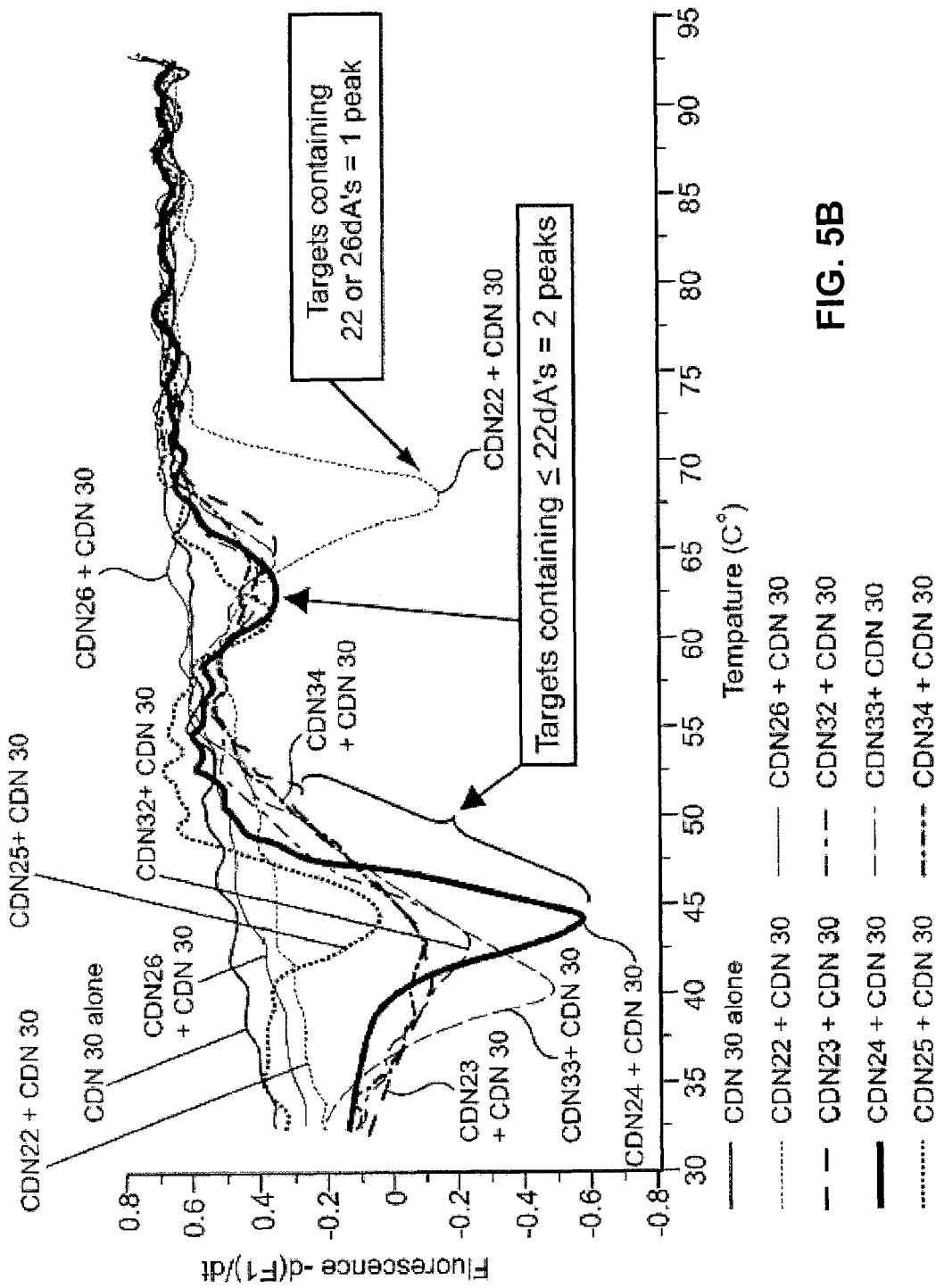
FIG. 5B provides this same data using a first derivative plot.

The results of these melting point analyses are shown in FIG. 5, panels A and B. FIG. 5, panel A is a melting curve plot of this data in which the y-axis represents absolute fluorescence (F1) and the x-axis represents temperature (° C.). FIG. 5, panel B is a melting curve plot of this data in which the y-axis represents relative fluorescence (−d(F1)/dT) and the x-axis represents temperature (° C.). The particular target nucleic acid associated with each trace is shown in the legend that is included in FIG. 5. As a negative control, the reaction mixtures of one set analyses lacked target nucleic acids. As shown in FIG. 5, panel B, target nucleic acids with repetitive nucleotide sequences having 22 dAs or fewer melted with two $T_m$ peaks each, while those with repetitive nucleotide sequences having 26 dAs melted with only one $T_m$ peak each.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting a mutation in a repetitive sequence within a target nucleic acid, the method comprising:
   providing at least one target nucleic acid, which target nucleic acid comprises at least one repetitive nucleotide sequence;
   binding in solution a probe nucleic acid comprising a fluorescent label to the target nucleic acid, which probe nucleic acid further comprises a first nucleotide sequence having a first and a second portion, wherein in the first portion, at least 80% of the nucleotides have exact pairing of bases with a non-mutant form of the repetitive nucleotide sequence; and wherein the second portion extends beyond the length of the repetitive nucleotide sequence and is not complementary to nucleotide sequences of the target nucleic acid that are adjacent to the repetitive nucleotide sequence; and wherein said first nucleotide sequence comprises at least one modified nucleotide;
   varying temperature to achieve dissociation of said probe and,
   detecting a bimodal dissociation, if any, of the fluorescent labeled probe nucleic acid from the target nucleic acid,
   correlating said detected bimodal dissociation with a mutation of the repetitive nucleotide sequence in the target nucleic acid.

2. The method of claim 1, wherein the first nucleotide sequence is longer than the non-mutant form of the repetitive nucleotide sequence.

* * * * *